United States Patent
Bukshpan et al.

(10) Patent No.: US 7,166,202 B2
(45) Date of Patent: Jan. 23, 2007

(54) MATRIXES, ARRAYS, SYSTEMS AND METHODS

(75) Inventors: Shmuel Bukshpan, Ramat Hasharon (IL); Gleb Zilberstein, Rehovot (IL)

(73) Assignee: Protein Forest, Inc., Watertown, MA (US)

( * ) Notice: Subject to any disclaimer, the term of this patent is extended or adjusted under 35 U.S.C. 154(b) by 384 days.

(21) Appl. No.: 10/198,071

(22) Filed: Jul. 16, 2002

(65) Prior Publication Data
US 2003/0102215 A1    Jun. 5, 2003

Related U.S. Application Data

(60) Provisional application No. 60/377,044, filed on Apr. 30, 2002, provisional application No. 60/340,698, filed on Oct. 29, 2001, provisional application No. 60/310,316, filed on Aug. 6, 2001, provisional application No. 60/305,802, filed on Jul. 16, 2001.

(51) Int. Cl.
*G01N 27/447* (2006.01)
*G01N 27/453* (2006.01)

(52) U.S. Cl. ........................ 204/459; 204/610

(58) Field of Classification Search ............... 204/459, 204/458, 609, 610, 468
See application file for complete search history.

(56) References Cited

U.S. PATENT DOCUMENTS

| | | | |
|---|---|---|---|
| 4,243,507 A | 1/1981 | Martin et al. | |
| 4,473,452 A | 9/1984 | Cantor et al. | |
| 4,900,414 A | * 2/1990 | Sibalis | 204/457 |
| 4,971,670 A | 11/1990 | Faupel et al. | |
| 5,082,548 A | 1/1992 | Faupel et al. | |
| 5,336,387 A | 8/1994 | Egen et al. | |
| 5,376,249 A | 12/1994 | Afeyan et al. | |
| 5,630,924 A | 5/1997 | Fuchs et al. | |
| 5,773,645 A | 6/1998 | Hochstrasser | |
| 5,916,428 A | 6/1999 | Kane et al. | |
| RE36,350 E | 10/1999 | Swedberg et al. | |
| 6,013,165 A | 1/2000 | Wiktorowicz et al. | |
| 6,017,696 A | 1/2000 | Heller | |

(Continued)

FOREIGN PATENT DOCUMENTS

EP    0 323 948 A2    7/1989

(Continued)

OTHER PUBLICATIONS

Bjellqvist et al. ("Isoelectric fousing in immobilized pH gradients: Principle, methodolgy and some applications," Journal of Biochemical and Biophysical Methods, 6(1982) 317-339).*

(Continued)

*Primary Examiner*—Alex Noguerola
(74) *Attorney, Agent, or Firm*—Pabst Patent Group LLP

(57) ABSTRACT

The present invention relates to matrixes, arrays, systems and methods for analyzing biomolecules by their isoelectric point, optionally, in combination with a second dimension analysis. The assortment of matrixes, arrays and systems provided herein are useful for causing a biomolecule under the influence of an electrical field to accumulate into an IEF buffer that comprises a pH value that is the same as the isoelectric point of the biomolecule. The methods of this invention are useful for, e.g., research and diagnostic purposes.

27 Claims, 22 Drawing Sheets

U.S. PATENT DOCUMENTS

| | | | |
|---|---|---|---|
| 6,103,533 | A | 8/2000 | Hassard et al. |
| 6,123,821 | A | 9/2000 | Anderson et al. |
| 6,136,173 | A | 10/2000 | Anderson et al. |
| 6,240,790 | B1 | 6/2001 | Swedberg et al. |
| 6,254,754 | B1 | 7/2001 | Ross et al. |
| 6,277,259 | B1 | 8/2001 | Guttman et al. |
| 6,329,209 | B1 | 12/2001 | Wagner et al. |
| 6,638,408 | B1 * | 10/2003 | Speicher et al. ............ 204/458 |

FOREIGN PATENT DOCUMENTS

| | | |
|---|---|---|
| EP | 1 044 716 A1 | 8/1997 |
| WO | WO 91/15773 A1 * | 10/1991 |
| WO | WO 91/17815 A1 * | 11/1991 |
| WO | WO 97/30346 | 8/1997 |
| WO | WO 00/04390 | 1/2000 |
| WO | WO 00/17631 | 3/2000 |
| WO | WO 00/31526 | 6/2000 |

OTHER PUBLICATIONS

Righetti, et al., "Preparative protein purification in a multi-compartment electrolyser with immobiline membranes," *J. Chromatography* 475: 293-309 (1989).

Becker, H., et al., "Planar Quartz Chips With Submicron Channels for Two-Dimensional Capillary Electrophoresis Applications," J. Micromech. Microeng. 8:24-28 (1998).

Daniels, M. and Landers, T. "Preparative-scale isoelectric purification of proteins without carrier ampholytes," Science Tools from Pharmacia Biotech 1(2):3-5 (1996).

Gygi, S.O. et al., "Evaluation of two-dimensional gel electrophoresis-based proteome analysis technology," Proc. Natl. Acad. Sci. USA 97(17):9390-9395 (2000).

Islam, R., et al., "A new approach to rapid immobilized pH gradient IEF for 2-D electrophoresis." Science Tools from Amersham Pharmacia Biotech 3(1):14-15 (1998).

Perrett, D., "Capillary Electrophoresis in Clinical Chamistry," Ann. Clin. Biochem. 36:133-150 (1999).

Righetti, P.G., "Isoelectric Focusing: Theory, Methodology and Applications," Laboratory Techniques in Biochemistry and Molecular Biology, Chapters 1 and 2; pp. 78-86, pp. 124-127 (1983).

Righetti, P.G., et al., "Protein Purification in Multicompartment Electrolyzers With Isoelectric Membranes," J. Chromatography B 699:105-115 (1997).

Zuo, X., et al., (Aug. 2000) Quantitative evaluation of protein recoveries in two-dimensional electrophoresis with immobilized pH gradients. Electrophoresis 21(14):3035-47.

Zuo, X., et al., (Sep. 2000) A method for global analysis of complex proteomes using sample prefractionation by solution isoelectrofocusing prior to two-dimensional electrophoresis. Anal. Biochem. 284:266-278.

Zuo, X., et al., (May 2001) Towards global analysis of mammalian proteomes using sample prefractionation prior to narrow pH range two-dimensional gels and using one-dimensional gels for insoluble and large proteins. Electrophoresis 22(9):1603-15.

Zuo, X. et al., (Jan. 2002) Comprehensive analysis of complex proteomes using microscale solution isoelectrofocusing prior to narrow pH range two-dimensional electrophoresis. Proteomics 2(1):58-68.

\* cited by examiner

MATRIXES, ARRAYS, SYSTEMS AND METHODS

FIELD OF THE INVENTION

The present invention relates to matrixes, arrays, systems and methods for preparing, sorting, amassing, or analyzing biomolecules based on separation in one dimension according to their isoelectric points in an electrical field, and optionally followed by a second analysis technique in a second dimension, and uses therefor.

BACKGROUND OF THE INVENTION

The basic principle behind isoelectric focusing or focusing in a pH gradient is that a charged molecule will become immobilized in a electric field when it migrates to a position in the pH gradient that is equal to its isoelectric point (zero net charge). This process occurs independently of the initial location of a specific protein in the solution. It is the result of the disappearance of the effective electrical charge of the protein when migrating to the region where pH is equal to pI.

Various techniques for determining the isoelectric point of a protein have been described. Typically, the protein of interest is injected or administered directly into a gel containing a pH gradient, wherein the pH gradient is parallel to the direction of the electric field, and the protein can only be separated from other proteins by traveling uni-directionally through many different pH environments before reaching a pH environment that is equivalent to its isoelectric point. These techniques suffer from the disadvantages that (1) they require a relatively long time to separate the protein because the velocity of the fraction tends to zero asymptotically; (2) they require relatively high voltages (typically 1000V and higher), and (3) they require a cooling mechanism. Traditional IEF methods are labor intensive, time consuming, non-standardized, expensive and not sensitive. Another practical limitation of traditional isoelectric focusing gels is that it is difficult to manufacture gels having incrementally small pH changes within a pH gradient to improve the linear dispersion of the proteins.

Two dimensional analysis of proteins that use the above described isoelectric focusing step suffer from the same problems. For example, Zuo et al., (2000) Analytical Biochemistry 284:266–278, describe the separation of proteins based on their isoelectric point by unidirectional travel through a pH range followed by sodium dodecyl sulfate polyacrylamide gel electrophoresis (SDS-PAGE). Becker, et al., (1998) J. Micromech. Microeng. 8:24–28 suggests the unidirectional travel of proteins through a pH range followed by a second dimension separation on a planar chip. See also, U.S. Pat. No. 6,254,754 (Ross).

Because of these limitations, only certain cell, lane, and matrix designs and orientations of the cells, lanes, and matrixes in a chamber, and certain systems for one and two dimensional analysis are possible thereby limiting the development of faster, more sensitive, more accurate, more flexible and less expensive methods for one and two dimensional analyses of samples, including automated, high throughput analysis systems. Better tools and methods for one and two dimensional analysis of biomolecule are useful for, e.g., drug development, medical research, and the pre-diagnosis and/or diagnosis of diseases. In particular, better tools and methods are need for proteomic analysis. The present invention solves these and other problems.

SUMMARY OF THE INVENTION

The present invention relates to matrixes, arrays, systems and methods for analyzing or preparing biomolecules by their isoelectric point in one dimension and, optionally, in combination with other methods for analysis. The assortment of cells, matrixes, arrays and systems provided herein have unique configurations and combinations of elements.

According to one embodiment, a biomolecule moves through the running buffer of a chamber of this invention and becomes trapped in an IEF buffer or a cell comprising an IEF buffer of this invention. According to another embodiment, a biomolecule that is trapped in an IEF buffer or cell of this invention remains trapped in the IEF buffer or cell while biomolecules having pI values that are not the same as the pH values of the IEF buffer are removed by alternating the direction of the electric field. If the IEF buffer or cell is closed so that the electrical current is preventing from exiting out the opposite side of its entry into the IEF buffer or cell, then, according to one preferred embodiment, the electric field is reversible. If the IEF buffer or cell is open, then the electrical field can be unidirectional. According to another embodiment of this invention, the movement of the biomolecule in the running buffer is increased by the convection heat generated by the electrical field.

According to another embodiment of this invention, the movement of the biomolecule in the running buffer is increased by a device that circulates the running buffer comprising the biomolecule across the IEF buffer (e.g., by stir bar, by pump or by the movement of the IEF buffer relative to the running buffer).

According to yet another embodiment, the pH range of the IEF buffer can be ultra-narrow (e.g, spanning 0.1 pH units or less; 0.02 pH units or less; or 0.01 pH units or less). According to one embodiment, the chamber comprising the running buffer further comprises a plurality of IEF buffers and/or cells that are isolated from each other either by physical separation or by a substrate that substantially prevents the movement of biomolecules directly from one IEF buffer/cell to another rather than through the running buffer. Thus, the biomolecule primarily moves through the running buffer to reach a different IEF buffer or cell. In another embodiment, the IEF buffers or cells have the same or different pH values. According to yet another embodiment, the present invention comprises a vast plurality of discrete, isolated IEF buffers having ultra-narrow, substantially non-overlapping pH ranges such that resulting image of the separated material is comparable positionally to an image from a traditional IEF gel but has greater resolution than a traditional IEF gel.

According to this invention, biomolecules of this invention can be separated as a single entity or as part of a complex based on their isoelectric point. For example, the biomolecule ("target biomolecule") can form a complex with another molecule that specifically recognizes it ("target recognition molecule"). The complex can be separated from other non-complexed biomolecules based on the isoelectric point of the complex using the matrixes, arrays, systems and methods of this invention.

According to one embodiment of this invention, an improved one- or two dimensional analysis method using a plurality of discrete, isolated IEF buffers with narrow pH ranges and steps, e.g., 0.1 pH units or less, is provided. More preferably, the pH range or step is 0.02 pH units or less. It is an object of this invention to provide improved one and two dimensional methods for analyzing biomolecule having pI values that are 0.02 pH or less units apart. According to one configuration of the system, diffusion of biomolecule from one cell into an adjoining cell is avoided, e.g., between cells that comprise IEF buffers with slightly different pH values, by using membranes or materials that are impermeable to the biomolecule. For example, each IEF buffer or cell comprising said IEF buffer can be physically separated, noncontinuous, discrete entities.

It is an object of this invention to provide an analysis method that allows the use of a high electric field at a low applied voltage, optionally avoiding the use of a kV range power supply. In one preferred embodiment, a device for reversibly directing an electrical field in and out of the IEF buffer in the cells and, optionally, device for circulating buffer around a plurality of cells simultaneously is used in the methods and systems of this invention. Another object of this invention is to provide an analysis method that requires little or no device for cooling the chamber. Yet another object of this invention is to provide a two dimensional matrix that requires minimal or no manipulation of the biomolecule during the first and second dimension separations, thereby saving time and effort and minimizing the loss of the biomolecule being tested.

Another embodiment of this invention provides an IEF technique suitable for use in combination with a second dimension analysis (e.g, high pressure liquid chromatography (HPLC), mass spectrometry, affinity chromatography, gel electrophoresis, etc. ). Yet another object of the invention is systems or methods capable of separating and/or purifying small or large quantities of a specific biomolecule, such as a protein or nucleic acid molecule. This invention also provides methods for detecting a target biomolecule complexed to a target recognition biomolecule. The target biomolecule can form a complex with the TB in environments that encourage or discourage complex formation. In one embodiment of the invention, a labeled target recognition biomolecule is placed directly into the IEF buffer cell, lane, or matrix prior to the introduction of the target molecule-containing sample.

Yet another embodiment of this invention is to provide systems and/or methods for one and two dimensional analysis that can be miniaturized and automated for high throughput analysis of samples for drug screening, medical research such as enhanced detection of biological response patterns for drug discovery, monitoring of drug therapies, genetic or proteome analysis, and clinical diagnosis, and diagnostics, e.g., proteome analysis. A system of this invention can be constructed to have automated interacting components, for example, titrators for filling of channels with pH solutions or gels (immobilines, ampholyte mixtures etc.), extractors for recovering biomolecule from the cells comprising IEF buffers, devices for staining the biomolecule, devices for detecting and scanning the biomolecule, devices for recording and analyzing the images. A system and/or method of this invention can be automated for high throughput screening of candidates useful for a desired drug effect.

This invention provides methods for enhancing detection of biomolecule in the response to various perturbations and stimuli, such as the response to a drug, a drug candidate or an experimental condition designed to probe biological pathways as well as changes in a animal or human that correspond to a particular disease or disease state, or to a treatment of a particular disease or disease state.

BRIEF DESCRIPTION OF THE DRAWINGS

FIG. 15 depicts examples of matrixes and an array according to this invention.

DETAILED DESCRIPTION

An IEF buffer comprises components that have a buffering capacity around a given pH value (buffering agent) or components that organize to form a pH gradient (e.g., ampholytes, immobilines or a combination of buffering agents). The IEF buffer according to this invention is in the form of a liquid or slurry or a gel such that a biomolecule can pass through IEF buffer unless the pI of the biomolecule is in the pH range of the IEF buffer. An IEF buffer according to this invention can comprise other components such as urea, detergent and a reducing agent as needed. See, e.g., Malloy, et al., *Anal. Biochem.* 280: pp. 1–10 (2000). It is desirable that the IEF buffers according to this invention are functionally stable under the influence of an electric field.

Figure 18:
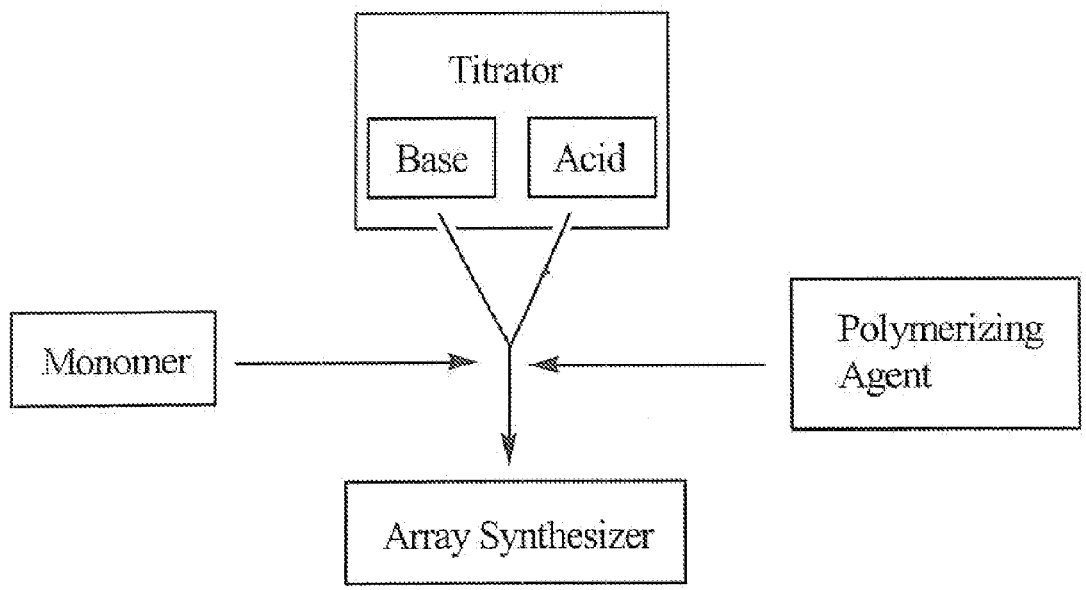
FIG. 18 is a schematic of an apparatus that can make an IEF buffer area on a matrix. A device is used to mix an acidic and basic solution to form an buffer having the desired pH value ("titrator"). The buffer is combined with a monomer (e.g., acrylamide) and polymerizing agent and loaded into another device ("matrix printer") that lays the IEF buffer in a desired position on the array.

The IEF buffer or cell comprising the IEF buffer can be formed by hand or by various devices. For example, the IEF buffer can be deposited (e.g, coated, printed or spotted) on the surface of a substrate or in a groove or channel of a substrate. The substrate can be a matrix as described below or a bead made of the same material as the matrix. According to one embodiment of this invention, the IEF buffer can be made by a device that mixes an acidic and basic solution to form an buffer having the desired pH value ("titrator"). The buffer is combined with a monomer (e.g., acrylamide) and polymerizing agent and loaded into another device ("matrix printer") that lays the IEF buffer in a desired position on the matrix. See, e.g., FIG. 18. These devices can be incorporated into an automated system of this invention.

Ampholines according to this invention are a set of various oligo-amino and/or oligocarboxylic acids that are amphoteric (i.e., positively charged in acidic media and negatively charged in basic media), soluble and have $M_r$ values from approximately 300 up to 1000 u. Ampholytes used in this invention can be prepared or purchased. For example, several carrier ampholytes are known in the art (e.g., pages 31–50, Righetti, P. G., (1983) *Isoelectric Focusing: Theory, Methodology and Applications*, eds., T. S. Work and R. H. Burdon, Elsevier Science Publishers B. V., Amsterdam; U.S. Pat. No. 3,485,736). Alternatively, purchased ampholytes include Ampholines (LKB), Servalytes (Serva), Biolytes or Pharmalytes (Amersham Pharmacia Biotech, Uppsala, Sweden).

Immobilines are non-amphoteric, bifunctional acrylamido derivatives of the general formula: $CH_2=CH-CO-NH-R$. Immobilines useful according to this invention can be prepared or purchased. For example, methods for synthesizing immobilines are known in the art (Bjellquist et al., (1983) *J. Biochem. Biophys. Methods.*, 6:317). The immobilines can be copolymerized with the acrylamide to form IPG's (immobilized pH gradients). IPG's can be prepared by methods known in the art or can be purchased.

pH gradients according to this invention can be formed by mixing amphoteric or non-amphoteric buffers. For example, such buffers combinations are described in Allen, R C et al., *Gel Electrophoresis and Isoelectric Focusing of Proteins: Selected Techniques*, Berlin:Walter de Gruyter & Co. (1984); and in U.S. Pat. No. 5,447,612 (Bier). Some IEF buffering agents include those are selected from the group consisting of 50 mM glycine, 14 mM NaOH; 50 mM HEPES, 12 mM NaOH; 50 mM THMA, 44.6 mM HCl; 52 mM citrate acid, 96 mM $Na_2HPO_4$; 50 mM BICINE, 18 mM NaOH; and 50 mM DMGA, 40 mM NaOH. The pH gradient created by the IEF buffer in each cell can have a narrow or a wide pH range (e.g., pH 6.8–pH 7.8 or pH 6.8-pH 12.8, respectively).

An IEF buffer of this invention can have an extremely narrow pH range, e.g. 5.50–5.60 (0.1 pH unit or less difference) or ultra narrow pH range, e.g., 5.52–5.54 (0.02 pH unit difference or less). This is possible because an IEF buffer according to this invention can be one buffering agent that has been adjusted to a certain pH value. In this case, the pH range of the IEF buffer is equivalent to the buffering capacity of the buffering agent around the pH value to which the buffering agent had been adjusted.

The term "interval" refers to the incremental difference in a pH value within the pH gradient created by the IEF buffer. The term "step" refers to the incremental difference in pH value between two different IEF buffers. For example, within one cell, the intervals can be as small as 0.02 pH units through the full pH range in that cell (e.g., pH 6.8, pH 7.0, pH 7.2, etc., in that cell). In another example, the pH "step" between an IEF buffer in cell #1 and cell #2 can be 0.1 pH unit. For example, the IEF buffer in cell #1 can have a pH gradient starting at pH 6.8 and ending at pH 7.8 and the IEF buffer in cell #2 can have a pH gradient starting at pH 7.9 and ending at pH 8.9 (i.e., pH 7.9 minus pH 7.8). The term "pH range" refers to the highest to the lowest pH values in an IEF buffer or a cell comprising an IEF buffer (e.g., pH 7.9-pH 8.9), or the difference between the highest and lowest pH values in a IEF buffer or a cell comprising an IEF buffer (e.g., 1.0 pH units). According to this invention, the intervals within a cell do not have to be uniform. Further, the pH steps between two cells of a plurality of cells do not have to be uniform. According to one embodiment, the matrix comprises IEF buffers or cells with IEF buffers having an extremely narrow or ultra narrow pH range and small pH steps between each cell.

According to one embodiment of this invention, the pH range of an IEF buffer in a cell is a narrow pH gradient, e.g., less than one pH unit or up to a few pH units. According to another embodiment, the pH gradient in the cell is over several pH units. According to one embodiment of this invention, the pH interval of an IEF buffer is 0.1 pH unit or less. In another embodiment, the pH interval of an IEF buffer is 0.02 unit or less. According to one embodiment of this invention, the pH steps between two or more IEF buffers are 0.01 units or less. According to another embodiment of this invention, the pH steps between two or more IGF buffers are 0.02 units or less.

Figure 1A:
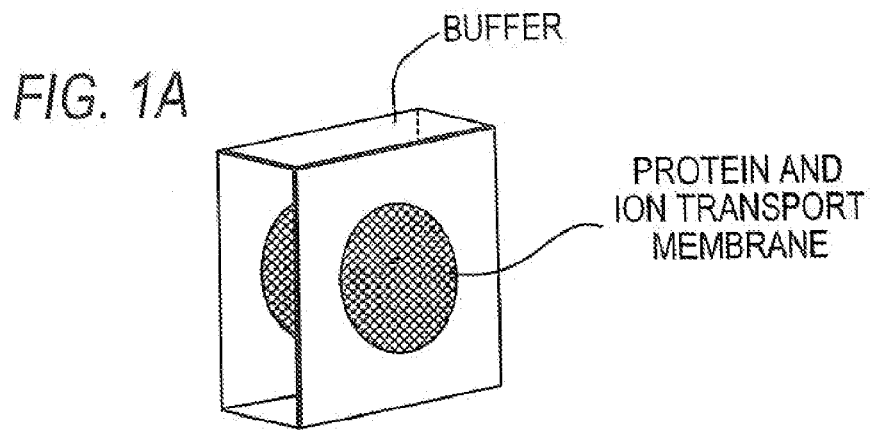
FIG. 1 depicts (A) a cell of this invention containing an IEF buffer and having a protein and ion permeable membrane on opposing sides of the cell; and (B) a matrix comprising a plurality of cells of this invention.
Figure 1B:
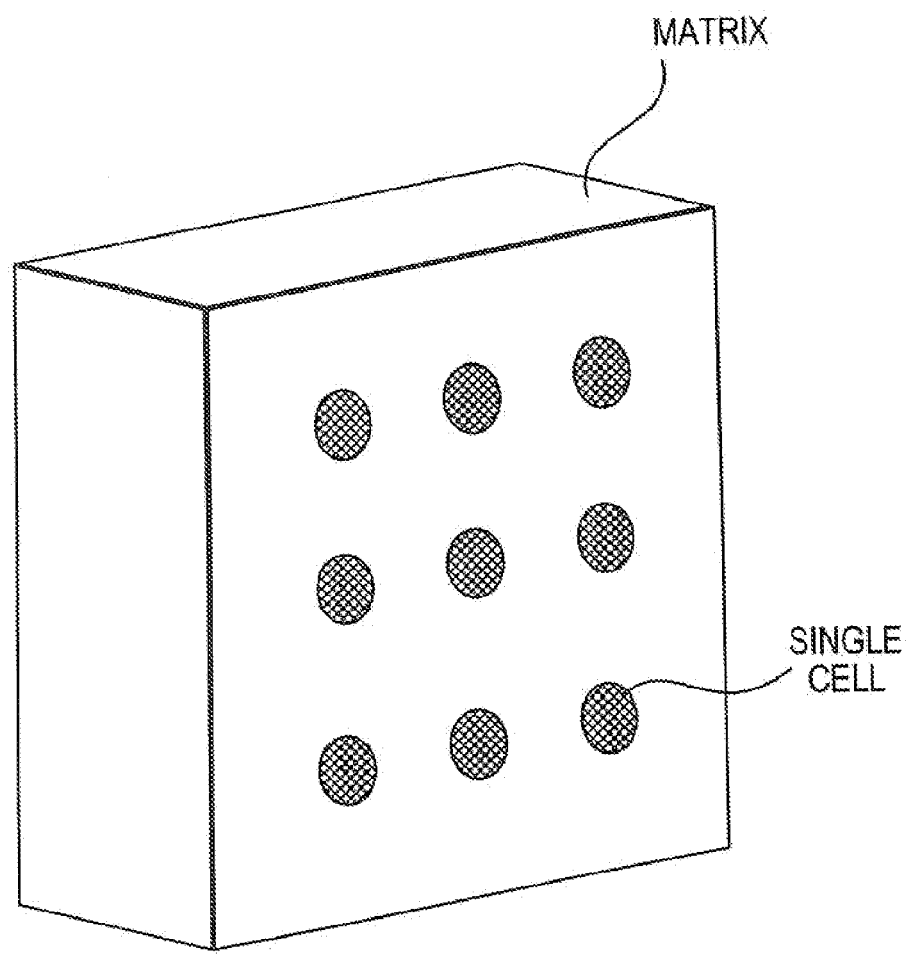

A cell according to this invention is a hollow structure that has an IEF buffer in it and/or integrated into a wall of it. The cell can have any shape including a sphere, a triangle, square, rectangle and a cylinder. A cell can have one or more walls depending on the shape of the structure. The walls of the cell have an inner side that faces towards the center of the structure and an outer side that faces towards the outside of the cell. See e.g., FIG. 1. Depending upon the desired use, a wall of a cell of this invention can be made of a membrane, mesh or solid that is biomolecule permeable, biomolecule impermeable, and/or penetrable or impenetrable by an electric field.

Some of the walls of the cell can be impenetrable to an electrical field. However, the cell walls should be constructed so that an electrical current can pass into the cell. An IEF buffer can be integrated into a wall of the cell. For example, a Whatman GF/D glass fiber filter disc can be immersed in acrylamide that is allowed to polymerize into a gel and then soaked in an IEF buffer. The disc can than be used to form a wall of the cell. Thus, a biomolecule can be trapped in a cell that has a wall soaked in an IEF buffer that is the same pH value as the pI value of the biomolecule.

If a sample comprising a biomolecule(s) of interest is added to the running buffer in the system, then at least one wall of the cell should be permeable to one or more of the biomolecule of interest. In one embodiment, all the walls of the cell are permeable to the biomolecule of interest. In another embodiment, all but one wall of the cell is biomolecule impermeable and/or impenetrable by an electric field. In a embodiment, the walls of the cell that face into and in the same direction as the electrical field in the first dimension are permeable to the biomolecule of interest.

According to an alternative embodiment, a wall or the walls of the cell can be substantially impermeable to the biomolecule of interest if the biomolecule of interest are being prepared by (1) adding a sample comprising the biomolecule of interest to the IEF buffer in a cell in the system and (2) allowing biomolecule and/or ions that are not of interest to migrate out of the cell. In this way, the cell can be used in the first dimension step in combination with the matrixes, arrays, systems and methods of this invention.

Figure 5A:
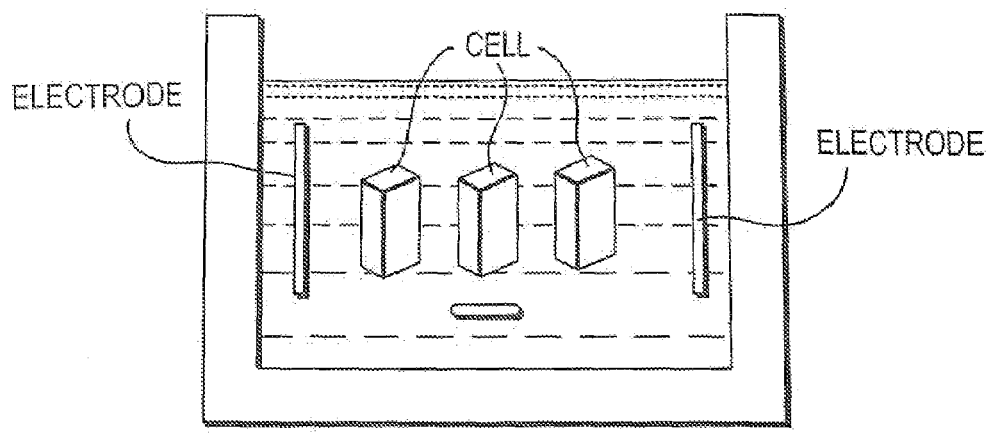
FIG. 5 depicts three apparatuses of this invention: (A) a plurality of cells are individually and randomly mounted on a insulated support in the running buffer in the chamber and between two electrode plates; (B) a plurality of cells are free floating in the chamber between two electrode plates; or (C) a plurality of cells are attached to each other and rotate between two electrode plates. A stir bar is used to circulate the running buffer. The direction of the electric field is reversible.
Figure 6A:
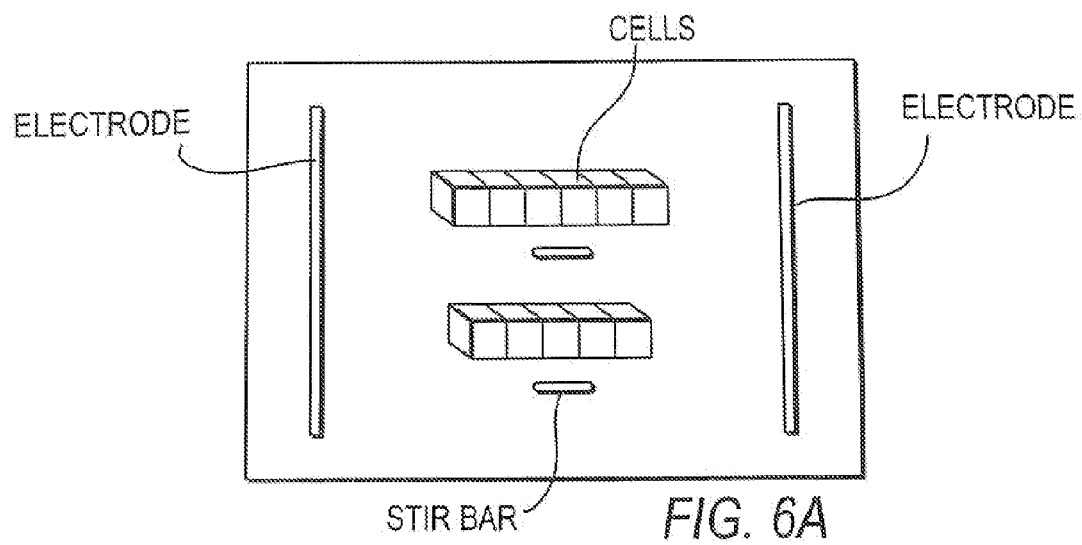
FIG. 6 depicts a top view of a chamber comprising a plurality of cells adjoined in series, separated by membranes that substantially maintain the pH range present in each cell, and arranged (A) in parallel or (B) perpendicular to the direction of the electrical field. A stir bar is used to circulate the running buffer. The direction of the electric field is reversible.
Figure 6B:
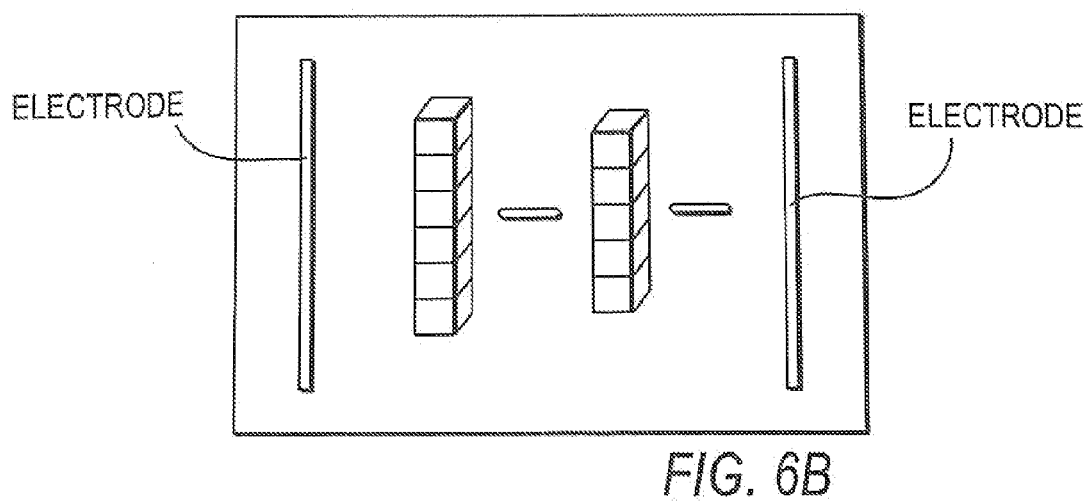
Figure 7:
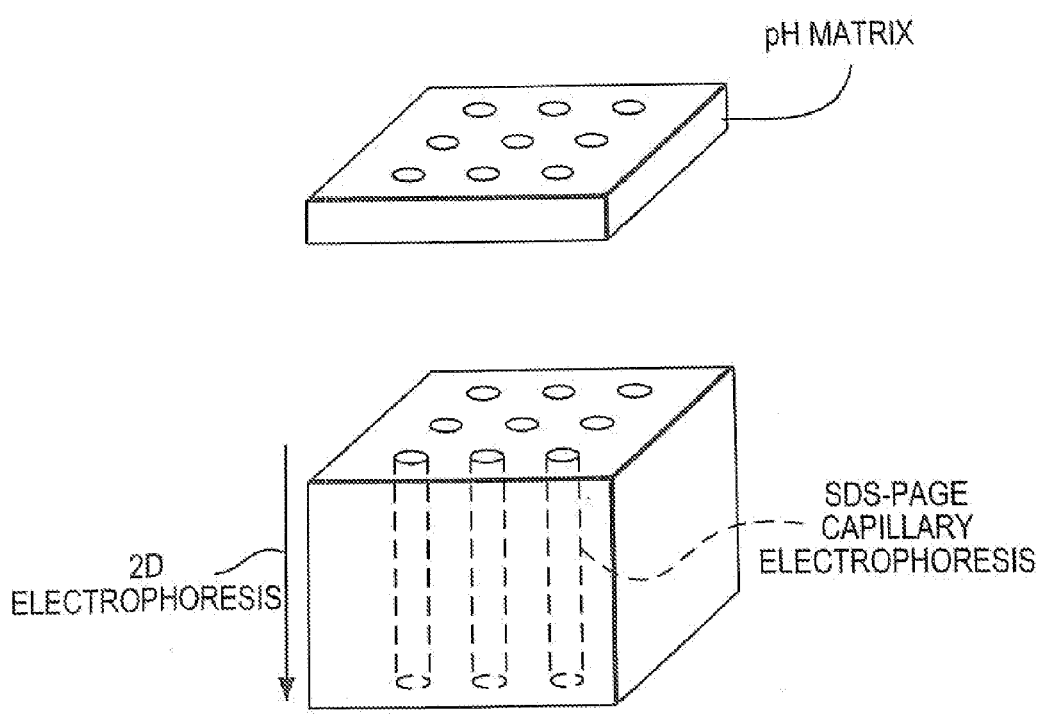
FIG. 7 depicts biomolecule in the cells of a matrix of this invention being subjected to SDS-PAGE capillary electrophoresis in a second dimension.
Figure 8:
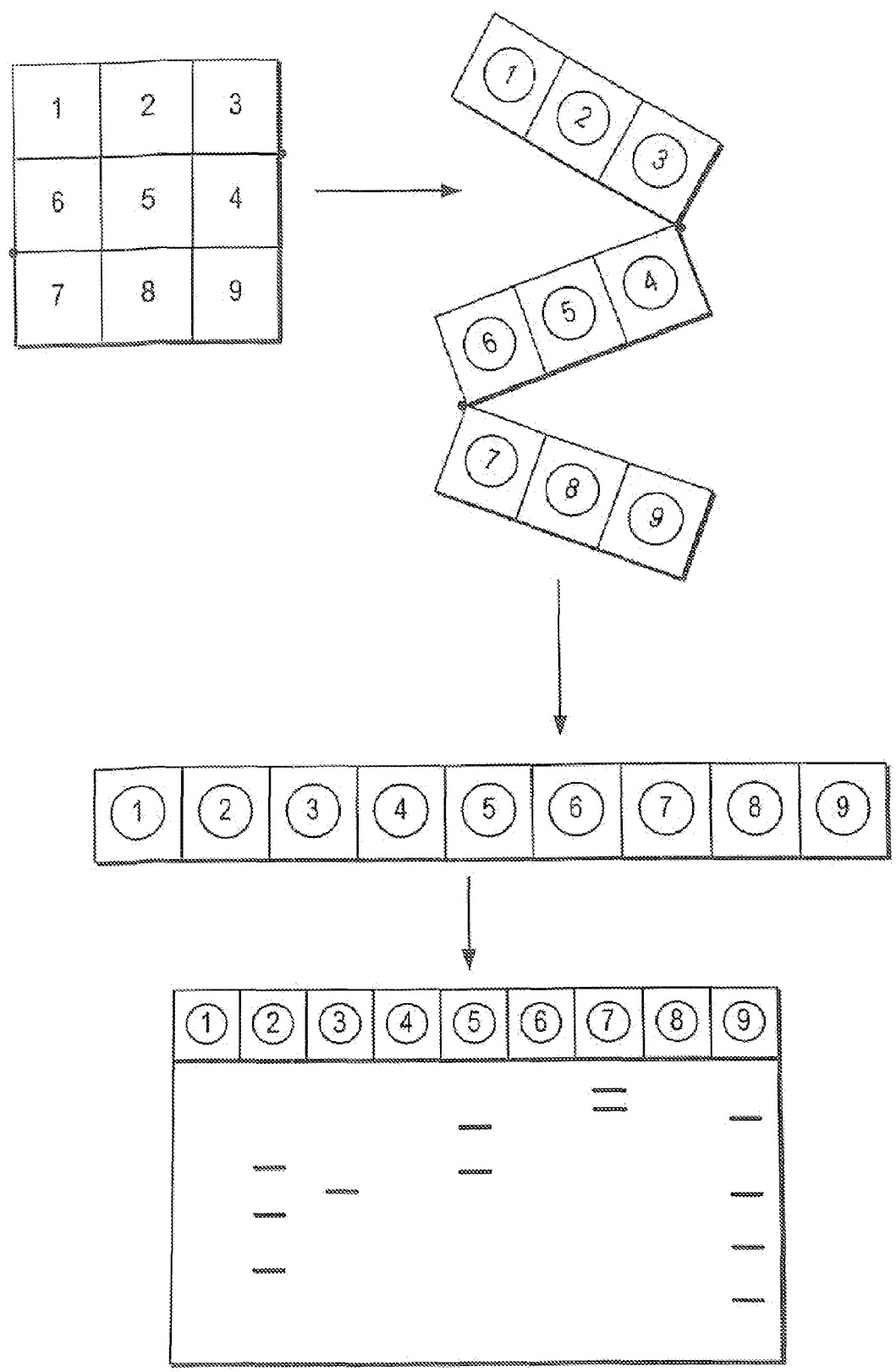
FIG. 8 depicts a matrix of this invention, wherein the cells are capable of being adjusted into a linear series for attaching to an SDS polyacrylamide gel for electrophoresis in a second dimension.

The cells can be arranged spatially in several ways. For example, the cells can be contiguously arranged, e.g., wherein a biomolecule-permeable or a biomolecule-impermeable material separates one cell adjoined to another. See e.g., FIGS. 6a and b. According to one embodiment, the IEF buffers or cells are "isolated" such that biomolecule substantially travel from one IEF buffer to another by migrating through the running buffer circulating around the IEF buffers or cells rather than through one IEF buffer directly into another IEF buffer or through the wall of one cell directly into another cell. See e.g., FIG. 5a, b or 2. According to one embodiment, the isolated cells are adjoined but have biomolecule-impermeable material separating them. See. e.g., FIG. 6. Alternatively, the isolated IEF buffers or cells are not adjoined. According to an embodiment of this invention, if the IEF buffers or cells are contiguously arranged, at least one of the walls of the IEF buffers or cells that is not adjoined to another IEF buffer or cell contacts the running buffer and is permeable to the biomolecule being tested. According to one embodiment of the invention, the IEF buffers or cells form part of a matrix. According to one embodiment, the IEF buffers or cells are not adjoined in series to each other when the cells are arranged in parallel to the electrical field of the first dimension.

The biomolecule-permeable or biomolecule-impermeable material can be a membrane depending on the desired result. According to one embodiment of this invention, the membrane can be prepared so that it has virtually no net charge in the electric field at the pores of the membrane. In an alternative embodiment, the pH of the membrane can be a pH value intermediate between the pHs on both sides of the membrane. This is desirable to minimize bulk fluid flow through the membranes caused by the presence or acquisition of an electrical charge on the membrane (electroendoosmosis). Depending on the desired result, membranes useful according to this invention include those described in U.S. Pat. No. 4,243,507 (Martin). Alternatively, membranes according to this invention can include membranes covalently bonded with immobilines as described in U.S. Pat. No. 4,971,670 (Faupel).

Figure 5B:
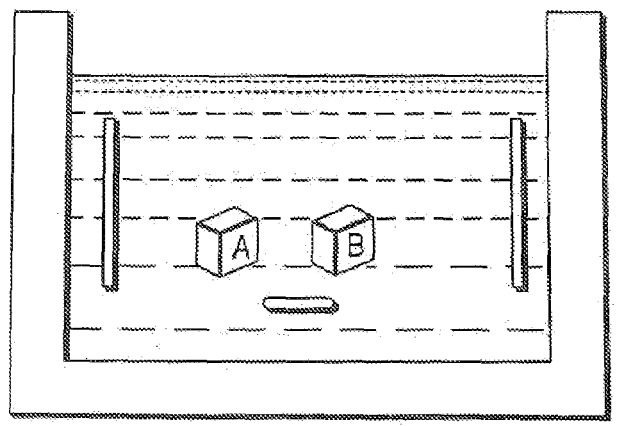
Figure 5C:
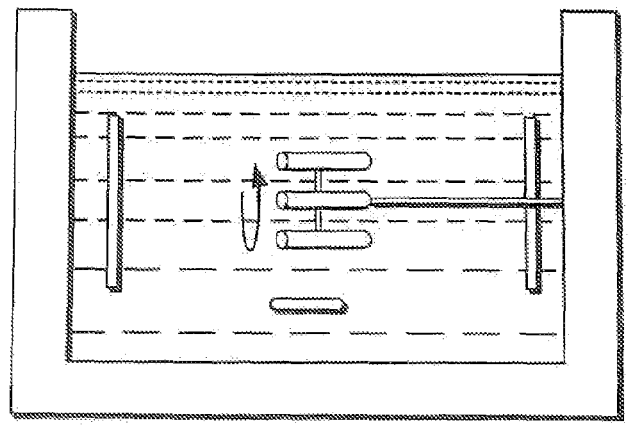

The cells according to this invention can be directly or indirectly attached to the chamber as long as the cells are capable of contacting the running buffer. For example, the cells may be attached directly to the bottom or sides of the chamber or mounted to the chamber by an insulating support. See e.g, FIG. 5a or 5c. Alternatively, the cells may be placed in a matrix that is attached to the chamber or attached to a post that is attached to the chamber. In yet another embodiment, the cells comprising an IEF buffer that is a buffering agent may float freely in the running buffer, but the cells should be distinguished to indicate the pH range of the IEF buffer in the cell. See e.g., FIG. 5b. According to this invention, the matrix or the individual cells can be attached to the chamber such that they rotate within the chamber.

The sensitivity of the methods and systems of this invention will increase as the size of the IEF buffer or cell decreases. According to one embodiment of this invention, the size of the IEF buffer or cell, particularly the length IEF buffer or cell, is as small as possible. The IEF buffer or cell length refers to the widest cross-section of the IEF buffer or cell that is parallel to the direction of the electric field in the second dimension. The IEF buffer or cell width refers to the widest cross-section of the IEF buffer or cell that is perpendicular to the direction of the electric field in the second dimension. In one embodiment of this invention, the cell length can be any size, e.g., 10 microns to 5.0 mm. In another embodiment of this invention, the cell width can be any size, e.g., 10 microns to 10.0 mm.

The lane according to this invention can be various sizes. According to one embodiment, the width of the lane is 20 microns to 1 mm. For example, the width of the lane can be 100 microns. According to another embodiment, the length of each lane is 3–10 mm.

The lane can comprise materials suitable for separation techniques (e.g., by size, shape, charge, affinity or combination thereof). Such as material can include those suitable for chromatography, electrophoresis such as SDS-PAGE, zone electrophoresis, affinity electrophoresis, capillary electrophoresis, and electro-chromatography. Accordingly, in one embodiment, the lane can be a capillary tube that is filled with chromatographic substances (e.g., liquid chromatography) or substances useful for electrophoresis (e.g, capillary zone electrophoresis, capillary gel electrophoresis using cross-linked and uncross-linked gels), and capillary isoelectric focusing. According to one embodiment, the second dimension is an electric field-mediated separation technique.

A lane according to one embodiment of this invention can comprise a gel-like material that is suitable for electrophoretic separation, e.g., U.S. Pat. No. 6,197,173 (Kirpatrick). The gel-like material can be comprised of monomers that have been polymerized. The gel can be denaturing or non-denaturing for the biomolecule of study. The gel can have various pore sizes. Accordingly, the lane can comprise additional components such as urea, detergent and a reducing agent as needed. See, e.g., Malloy, et al., *Anal. Biochem.* 280: pp. 1–10 (2000). The lane itself can comprise an IEF buffer for further separation of the biomolecule that have accumulated in the IEF buffer of the first dimension. Alternatively, a lane that comprises an IEF buffer can be converted into an SDS-containing gel by the addition of SDS to the running buffer, hence the biomolecule can separate in the second dimension based on molecular weight.

According to one embodiment, the lane is premade to comprises sodium dodecylsulfate (SDS) and polyacrylamide gel. According to another embodiment, the length of the lane is sandwiched between two biomolecule impermeable layers. According to a further embodiment, if the lane comprises SDS and polyacrylamide gel, the lane can be sandwiched between a matrix layer and another layer, wherein both layers can be biomolecule impermeable and ion impermeable as long as an electrical field can penetrate the lane and direct an electric field down the lane away from the IEF buffer. See e.g., FIG. 16

Figure 19:
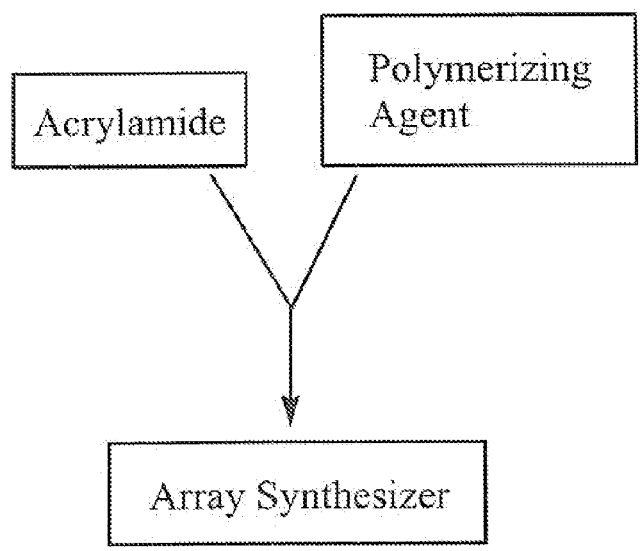
FIG. 19 is a schematic of an apparatus that can make the lanes on a matrix. An acrylamide solution and a polymerizing agent is loaded into a device ("matrix printer") that lays lanes in a desired position on the array.

The lane can be formed by hand or by various devices. For example, an acrylamide solution and a polymerizing agent can be loaded into a device ("matrix printer") that lays lanes in a desired position on an array. See, e.g., FIG. 19. A modified office inkjet printer is one example. Such devices can be incorporated into an automated system of this invention.

Various monomers can be used in addition to the conventional acrylamide/bis-acrylamide solution or agarose solutions to make a gel for use in the first and/or the second dimension steps according to this invention. It is known in conventional chemically-polymerized gels to use hydroxyethylmethacrylate and other low-molecular weight acrylate-type compounds as monomers; these have been commercialized as "Lone-Ranger" gels. Use of polymers substituted with one or more acrylate-type groups has also been described in the literature (Zewert and Harrington, *Electrophoresis* 13: pp. 824–831, (1992)), as especially suitable for separations in mixed solvents of water with miscible organic solvents, such as alcohol or acetone. Gel-forming monomers can also be any substantially water-soluble molecule containing a photo-polymerizable reactive group, in combination with a material which can form cross-links, provided that the combination, once polymerized, forms a gel suitable for the particular type of electrophoresis.

Exemplary materials include acrylamide, in combination with methylene-bis-acrylamide or other known crosslinkers; hydroyethylmethacrylate and other low-molecular weight (less than about 300 daltons) derivatives of acrylic acid, methacrylic acid, and alkyl-substituted derivatives thereof, such as crotonic acid; vinyl pyrrolidone and other low-molecular weight vinyl and allyl compounds; vinylic, allylic, acrylic and methacrylic derivatives of non-ionic polymers, including such derivatives of agarose ("Acrylaide" crosslinker, FMC Corp.), dextran, and other polysaccharides and derivatives, such as cellulose derivatives including hydroxyethyl cellulose; polyvinyl alcohol; monomeric, oligomeric and polymeric derivatives of glycols, including polymers of ethylene oxide, propylene oxide, butylene oxide, and copolymers thereof; acryl, vinyl or allyl derivatives of other water-compatible polymers, such as polyHEMA (polyhydroxyethyl acrylic acid), polymeric N-isopropyl acrylamide (which is temperature-sensitive), maleic-acid polymers and copolymers, partially hydrolysed EVAC (polymer of ethylene with vinyl acetate), ethyleneimine, polyaminoacids, polynucleotides, and copolymers of the subunits of these with each other and with more hydrophobic compounds such as pyridine, pyrrolidone, oxazolidine, styrene, and hydroxyacids. The polymerizable materials need not be entirely water-soluble, especially when solvents or surfactants are included in the gel-forming solution.

Methods for making polymerizable derivatives of common polymers are known in the art; for example, addition of allyl glycidyl ether to hydroxyl groups is known, as is esterification of hydroxyls with acids, anhydrides or acyl chlorides, such as acrylic anhydride. Amines are readily derivatized with acyl anhydrides or chlorides. Many of the derivatized polymers described above will contain more than one reactive group, and so are self-crosslinking. Addition of a crosslinking agent, which contains on average more than one reactive group per molecule, is required for formation of gels from monomers which have only one reactive group, such as acrylamide. These include, in addition to multiply-derivatized polymers, methylene bis-acrylamide, ethylene glycol diacrylate, and other small molecules with more than one ethylenically-unsaturated functionality, such as acryl, vinyl or allyl.

Candidate non-acrylamide monomers can include, e.g., allyl alcohol, HEMA (hydroxyethyl(meth)acrylate), polyethylene glycol monoacrylate, polyethylene glycol diacrylate, ethylene glycol monoacrylate, ethylene glycol diacrylate, vinylcaprolactam, vinylpyrrolidone, allylglycidyl dextran, allylglycidyl derivatives of polyvinylalcohol and of cellulose and derivatives, vinyl acetate, and other molecules containing one or more acryl, vinyl or allyl groups.

An IEF/lane unit according to this invention is an IEF buffer or a cell comprising an IEF buffer together with a lane according to this invention. In one embodiment, the IEF/lane unit is premade such that the IEF buffer is contacted to the lane. See e.g., FIG. 16D. In another embodiment, the IEF/lane unit can be premade so that the IEF buffer and lane are separate, but can be caused to be connected to each other. For example, the IEF buffer and lane can be movable in the matrix so that they can be forced together at the desired time. In another example, the IEF buffer and lane can be connected via a gel plug that joins the two together. When an IEF buffer or cell is connected to a lane, the connection between the IEF buffer or cell and lane must be permissive for transfer of biomolecule of interest or of study.

Figure 15A:
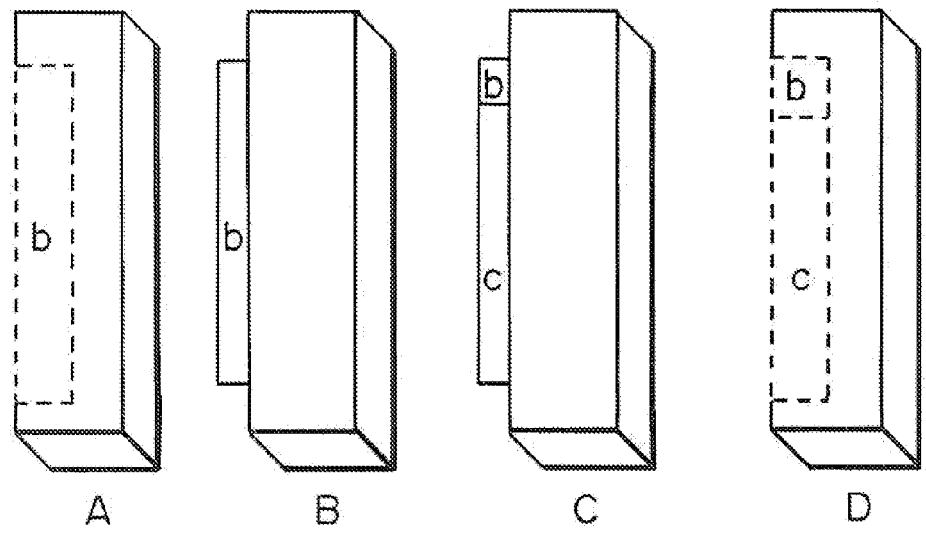
FIG. 15A depicts side views of four examples of matrixes of this invention each containing an IEF buffer ("b"). Matrixes A and D have grooves comprising IEF buffer in it. Matrixes B and C have IEF buffers set on the surface of the matrix. Matrixes C and D have an area designated "c," which is a lane. The matrixes A–D can be used in combination with a second layer in the system according to this invention for two dimensional analysis. The direction of the electrical field for the isoelectric focusing step is indicated as "E1." A portion of "b" in matrix A and B can also serve as a lane for the second dimension separation according to this invention, (e.g., by adding sodium dodecyl sulfate to the running buffer during the second dimension separation). According to another embodiment of this invention, matrixes A–D can be rotated 90 degrees in any direction in the same E1 field during the isoelectric focusing step (not shown).
Figure 15B:
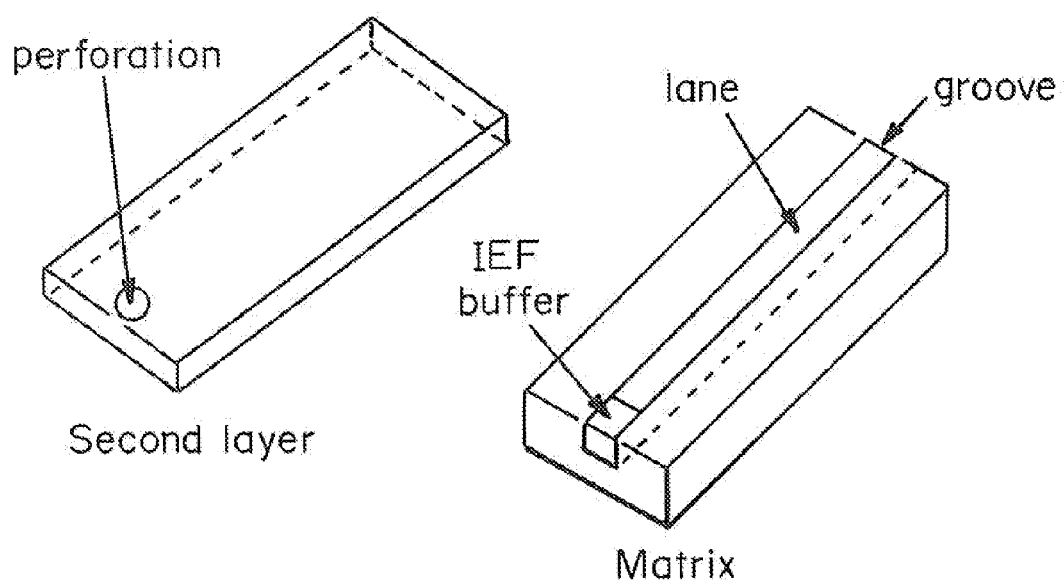
FIG. 15B depicts an array wherein a second layer comprising a perforation can be placed on a matrix such that the IEF buffer in the matrix is capable of contacting a running buffer during the separation in the first dimension.
Figure 16A:
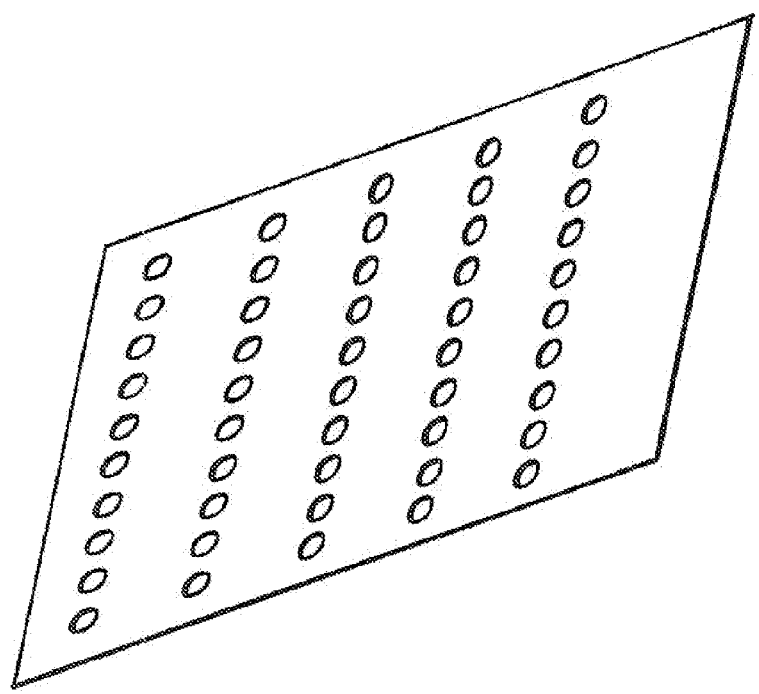
FIG. 16 relates to an example of array of this invention. (A) is a top view of an example of a second layer of an array. In this example, the second layer is manufactured from a material that is impermeable to biological molecules but is permeable to ions in the running buffer. (B) is a top view of an example of a matrix according to this invention. The matrix comprises a rectangular groove that is filled with gel to form the lane and a circular groove that is filled with IEF buffer. (C) is a top view of the second layer of (A) aligned on top of the matrix of (B) so that the IEF buffer is exposed through the perforation in the second layer. (D) is an side view of one of the IEF/lane units of the array of (C). (E) is an enlargement of a side view of a portion of the array of (C) (dotted circle). The top layer is the second layer (A) and the bottom layer is the matrix (B).
Figure 16B:
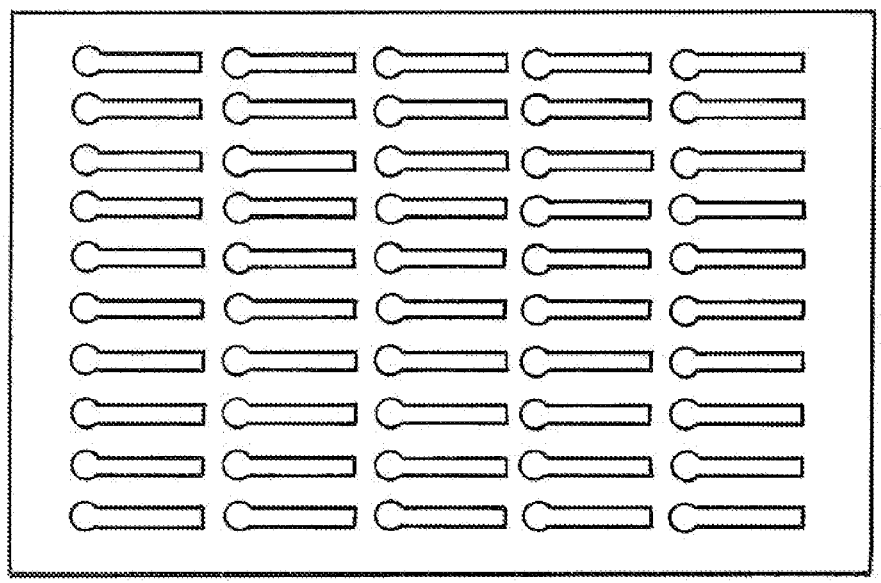
Figure 16C:
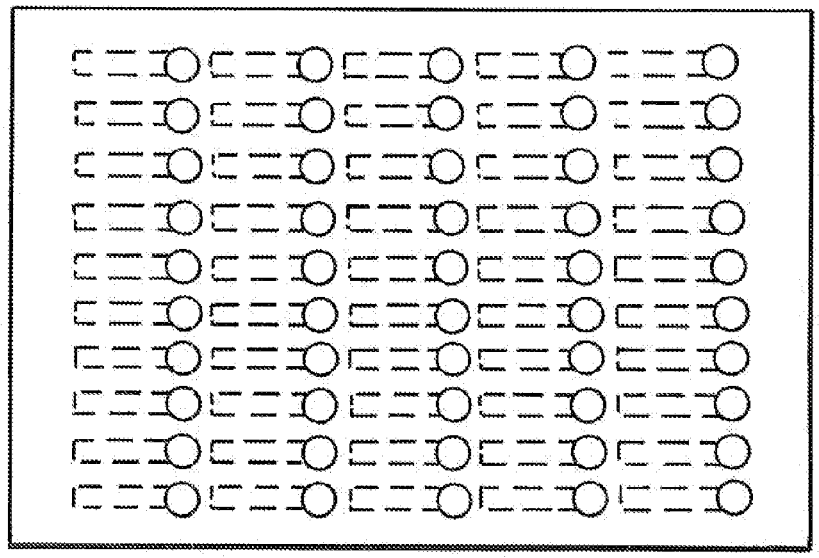
Figure 16D:
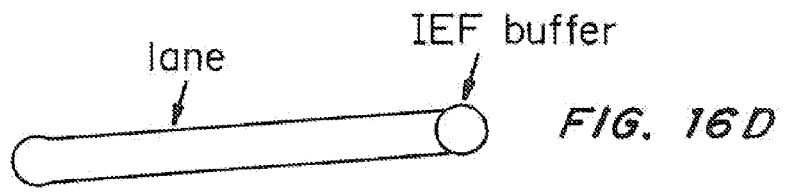
Figure 16E:
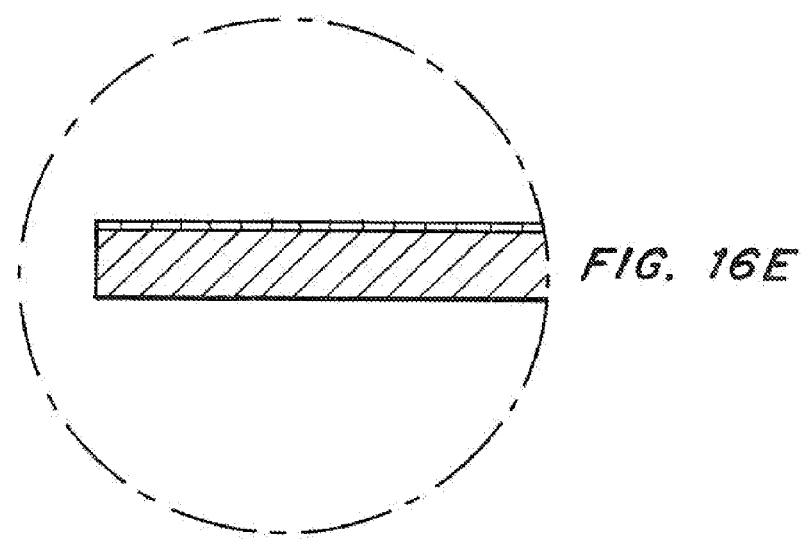

A matrix (or matrix layer) according to this invention is a solid material or a semi-solid material, e.g, a ceramic, a glass, polystyrene, poly(methyl methacrylate) such as lucite, or a gel, that comprises one or a plurality of cells and/or IEF/lane units. According to one embodiment, the material forming the matrix is poorly conductive. According to another embodiment, the matrix is, in part or in whole, made of a material that is biomolecule impermeable and ion impermeable (BIA) to contact the length of the lane. An IEF/lane unit can be set on the surface of the matrix e.g., as a gel, FIG. 15, matrix B or C, can be set in a groove etched in the matrix layer or can extend through the matrix layer as long as the IEF buffer or cell can contact the running buffer in the first dimension. According to one embodiment of the invention, if the IEF buffer, cell or lane extends through the matrix, then, one of the sides of the IEF buffer, cell or lane that contacts the running buffer is covered with a biomolecule impermeable layer. The matrix can be movable or within the chamber.

The matrix can be made, for example, by a drilling hole(s) through one side of the matrix out through to the opposing side of the matrix, filling the channel with an IEF buffer and sealing the openings in the channel with an ion-permeable, protein-permeable membrane. Alternatively, the channels can be filled with a polymer, such as agarose or polyacrylamide gel, mixed with an IEF buffer that solidifies into a gel having a particular pH range. The cells in the matrix can also be made by creating a groove or a plurality of grooves, which do not extend through the opposing side of the matrix, e.g., FIG. 15, matrix A or D. The grooves can be made on any side of the matrix. According to one embodiment, the grooves are on one side of the matrix. The grooves can be filled with one or a plurality of IEF buffers.

According to one embodiment of the invention, the IEF buffers or cells are isolated so that biomolecule substantially travel from IEF buffer or cell to another IEF buffer or cell via the running buffer instead of directly between each other. When a cell extends through one side of the matrix to the opposite side of the matrix, it can be referred to as a channel. The channels in the matrix are typically arranged in parallel to each other. According to one embodiment, the matrix layer comprises a plurality of identically orientated IEF/lane units. According to another embodiment, the plurality of identically orientated IEF/lane units can be arranged in parallel and/or in tandem to each other. According to another embodiment, the matrix or chip of this invention is pre-designed to include a subset of cells comprising IEF buffers for use in creating a calibration curve or having a standard to compare with the results from the other cells, e.g., FIG. 15. According to another embodiment, the matrix or chip of this invention is pre-made diagnostic tool comprising a pre-selected set of IEF buffers having pH values that correspond to the pIs of known biomolecule of interest (e.g., a biomolecule marker for a disease state) or series of biomolecule indicative of a disease state.

Figure 22:
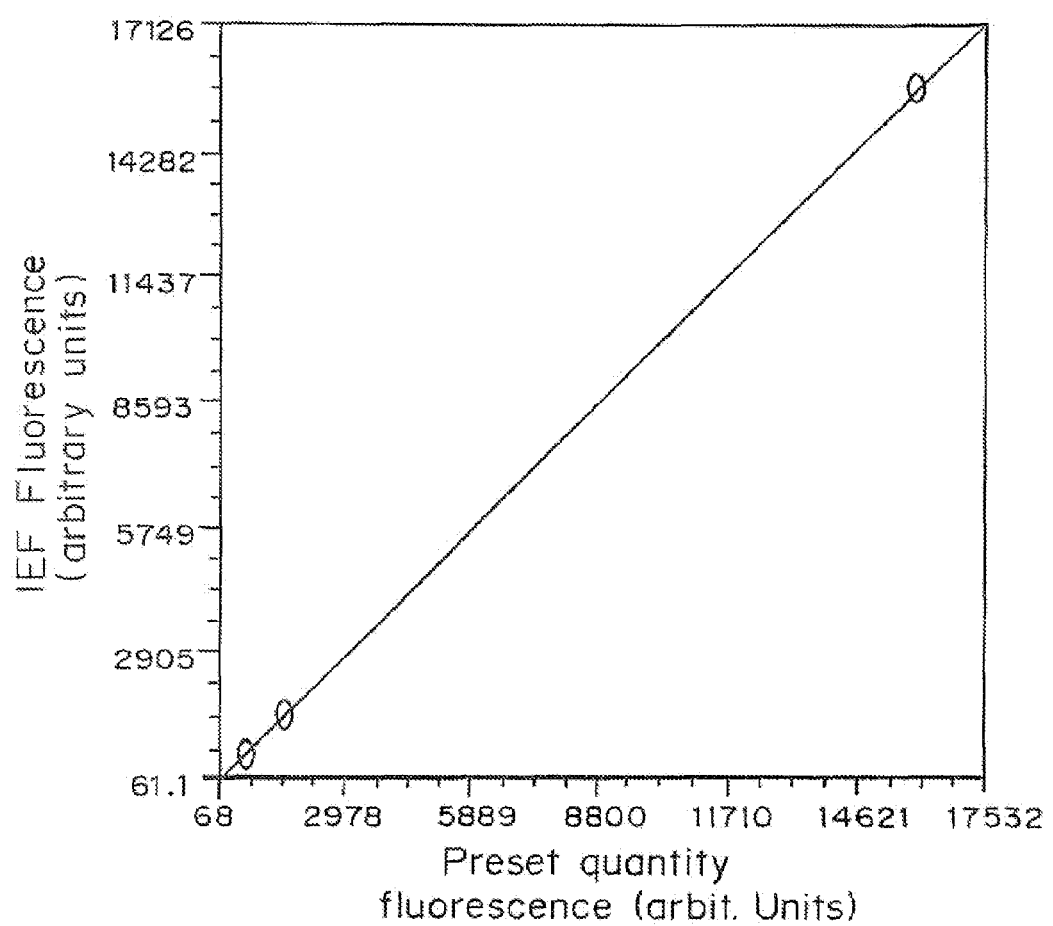
FIG. 22 is a chart demonstrating the efficiency of separation within the IEF system by plotting calibrated fluorescence as determined by the dispersion of a labeled protein through a gel vs. the observed fluorescence of a labeled antibody after 10 minutes of isoelectric focusing. The numbers represent the total number of protein molecules in the sample, demonstrating near 100% efficiency in protein separation.

Calibration curves according to this invention are useful for determining the amount of a target biomolecule ("TB") in a sample. A quantitative calibration curve can be generated by mixing in known concentrations of known biomolecule or complexes comprising known biomolecule and evaluating the accumulation of the known biomolecule or complexes in cells having the appropriate IEF buffer. Preferably, if the TB and/or target recognition molecule ("TRM") is commercially available or readily obtainable, the commercially available or readily obtainable TB is used as the known biomolecule or is contacted with the commercially available or readily obtainable TRM to form the complex for the calibration curve. The known biomolecule can be labeled or can be present in a complex that is labeled. Preferably, the same label is used in the process of generating the calibration curve and testing the sample. The concentration of the known biomolecule or complex that was added to the running buffer can be graphed against the quantity of the signal in the cell in which it accumulated. The graph can be used as a means for extrapolating the concentration of the TB in a sample based on the quantity of the signal in the cell in which it accumulated. See, e.g., FIG. 22.

After the complexes are separated into each cell, the complex can be subjected to analysis in a second dimension, i.e. analysis outside of the cell. For example, second dimension analysis include methods of analysis such as SDS PAGE, mass spectrometry, and HPLC chromatography.

The electrical field in the first dimension should be able to pass into the IEF buffer. The angle between the direction of electrical field and the matrix can be between +90 to −90 degrees relative to each other so long as the electrical field can pass into the IEF buffer in the channels. In one embodiment, the angle is +90 degrees. In another embodiment of this invention, the electric current is not reversible and flows in a single direction across a system wherein the IEF buffer and cell are non-adjoined and walls permeable to the biomolecule in question are oriented perpendicular to the direction of the electric current with the sample added directly to the running buffer. In another embodiment, said system is provided with a stirring means, for instance, a magnetic stir bar. In still another embodiment of this invention, the convection current generated within the running buffer during the experiments are the sole means by which the system is stirred.

Figure 11:
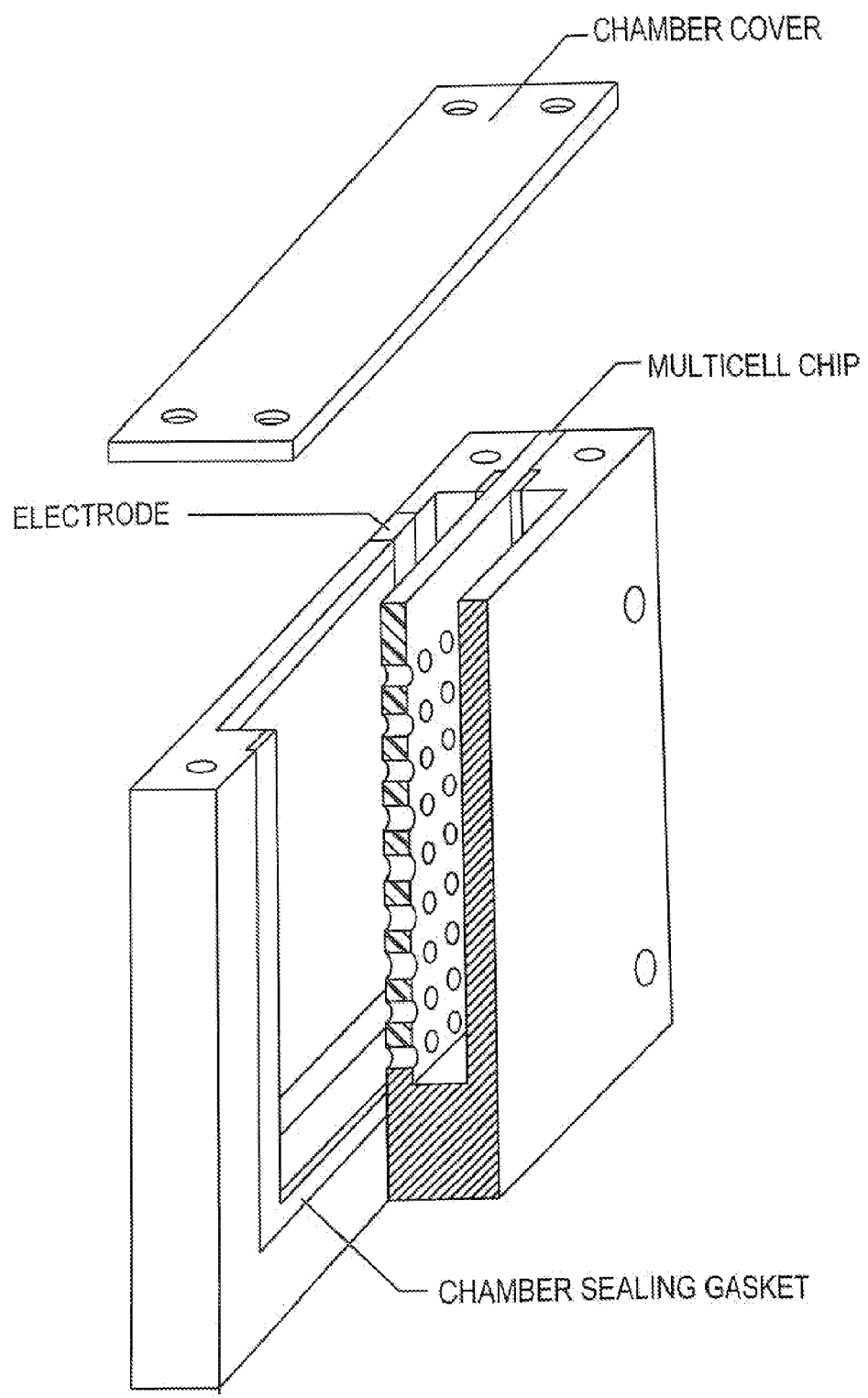
FIG. 11 is an image of a chamber comprising a multicell chip located between two electrode plates according to one embodiment of this invention. The chamber can be attached to a power supply capable of reversing the polarity of the electrical field. The chamber can further comprise a mechanism(s) for stirring the running buffer in both compartments on either side of the multicell chip.
Figure 12:
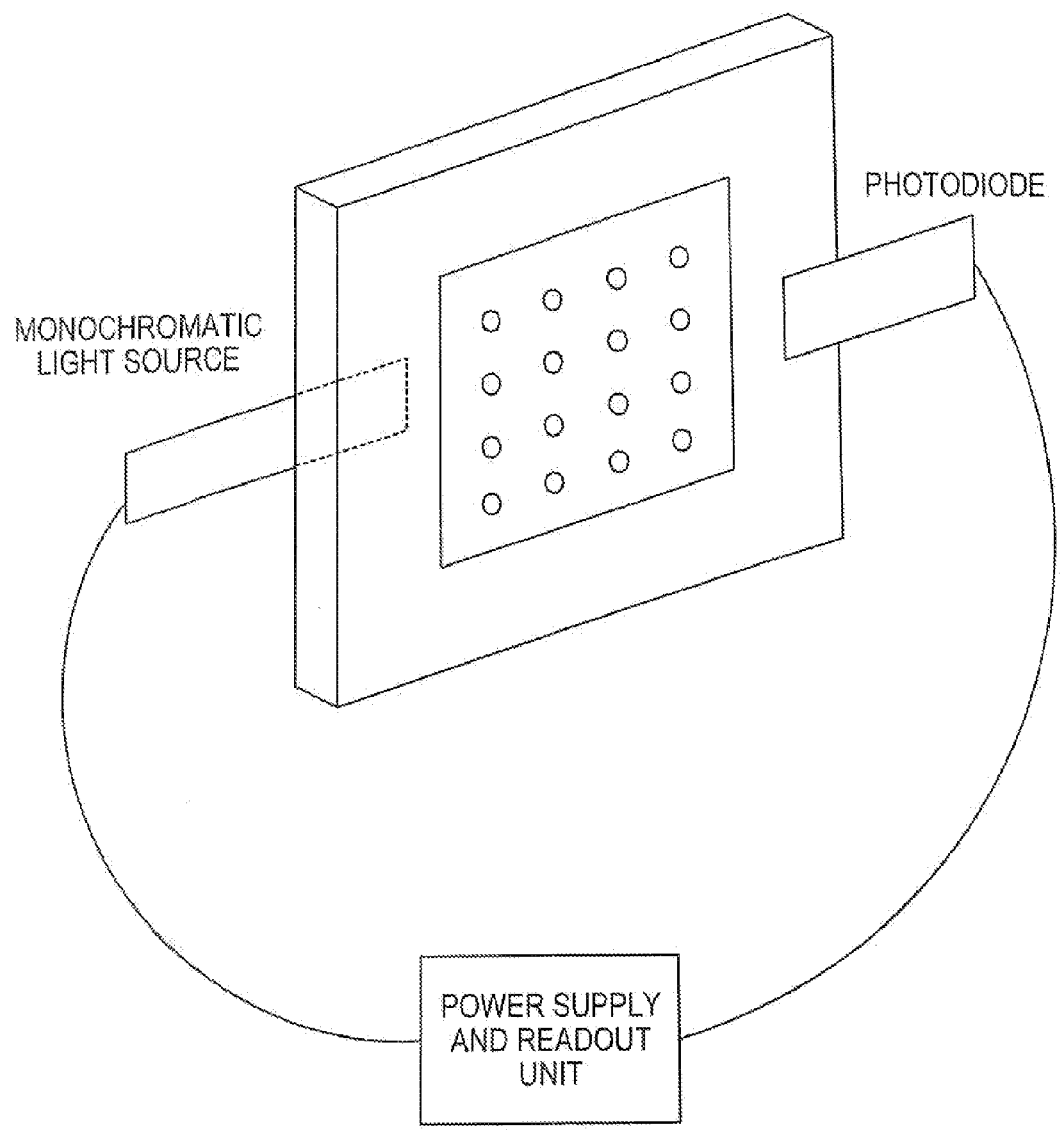
FIG. 12 is an image of a detection device for a multicell chip according to one embodiment of this invention. After one or more complexes are received into a plurality of cells in the chip, the chip can be placed in a detection device. Fluorescently labeled complexes in a multicell chip can be stimulated by a light source (e.g., monochomatic light source) for detection, then the light emitted from the label can be captured by a photodiode, converted into an electronic signal (read out unit), and analyzed by a computer. The chip can be encased in a holder that is movable relative to the light source or diode. Alternatively, the light source and diode can be moveable relative to the chip.

In one embodiment, for high throughput screening of samples, it is useful if the matrix comprising the cells is a small chip-like structure. The chip can be made of any material that can be micro-fabricated, e.g., dry etched, wet etched, laser etched or machined, molded or embossed, to have desired miniaturized surface features. The chip can be a polymer, a ceramic, a glass, a composite thereof, a laminate thereof, or the like. The use of micro-fabrication techniques such as, but not limited to, bulk etching, surface micro-machining, thick film processing, laser ablation, laser etching, molding and embossing, in the practice of the invention allows for a high degree of precision in the alignment of micro-scale components and structures, e.g., E. W. Becker et al., (1986) Microelectronic Engineering 4:35–56. In one embodiment, the chip comprises a plurality of cells, wherein two or more cells have different IEF buffers. See e.g., FIG. 11. In a another embodiment, the pH values of the IEF buffers of the subset of cells are not the same as the pH of the IEF buffers of the cells in which the complexes comprising the TB are accumulating.

The dimensions of the matrix can be, for example, 1×1 cm to 10×10 cm. According to one embodiment, the matrix is 5×5 cm or 4×10 cm, depending on the number of lanes, the length of those lanes and the spacing between them. According to one embodiment, the thickness of the matrix is 1 mm.

An array according to this invention is a matrix that additionally comprises a second layer. The second layer generally functions to cover one side of the lane to prevent substantial amounts of biomolecule in a sample from localizing in the lane during the IEF separation step but allows an electrical field to penetrate the lane during the second dimension step. Accordingly, the second layer comprises a lane screening area (LSA) that is the same length and width of the lane or larger, wherein the LSA is impermeable to a biomolecule and is permeable to ions. The second layer can be made entirely of the LSA material or it can be constructed to have portions of LSA material with the dimensions of the lane. According to one embodiment of this invention, the LSA is not conductive. According to another embodiment, the lane is sandwiched between the matrix layer and the LSA.

Materials that are biomolecule impermeable, yet ion permeable are known in the art, e.g., cellophane, polyether sulfone, nylon, cellulose acetate, polyvinylidene fluoride (PVDF), perfluorosulphonate cation exchange membranes (e.g., Nafion membranes) and other perflorinate ion exchange membranes.

Figure 17:
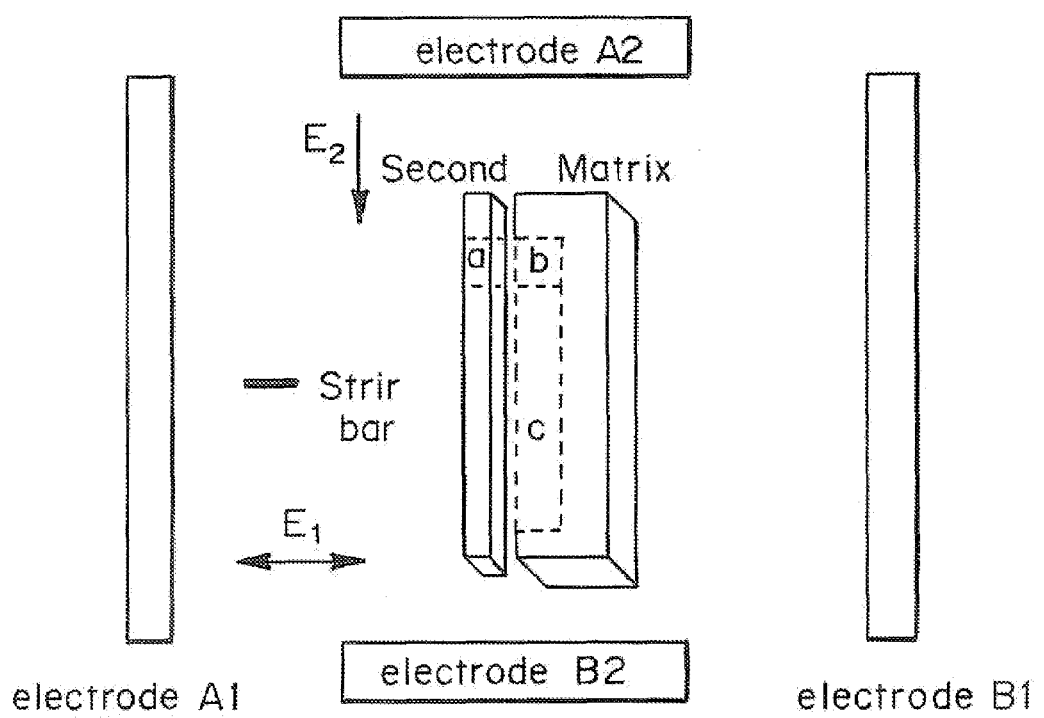
FIG. 17 depicts top view of an example of a system of this invention comprising an array according to this invention in a chamber comprising running buffer. A stir bar is in the chamber to allow circulation of the biomolecule across the IEF buffer(s) or cells in "b." Electrodes A1 and B1 create an electric field that periodically reverses direction during the isoelectric focusing step.

A second layer according to this invention may optionally additionally comprise a perforation through the plane of the second layer. The perforation an be arranged so that the perforation is positioned over the IEF buffer or cell comprising the IEF buffer. The function of the perforation is to allow biomolecule in the sample have access to the IEF buffer or cell during the IEF separation step. See, e.g., FIGS. 16*a* and *b*. The second layer can be detachable from the matrix, permanently attached to the matrix or not connected to the matrix at all. Examples of arrays according to this invention can be seen in FIGS. 15B and 16C and the combination of the "second" and "matrix" in FIG. 17.

A chamber according to this invention is a container comprising a running buffer. See e.g., FIG. 2. According to one embodiment of this invention, the chamber is designed to hold a small volume of running buffer, i.e., the minimal amount needed to contact the cells and electrodes so that an electrical field can pass into the IEF buffer or cell and the lane. According to another embodiment of this invention, the outside of the chamber further comprises connectors to allow electrical current to pass through into the chamber to the electrodes. According to yet another embodiment of this invention, the chamber is disposable.

A running buffer according to this invention is a solution in the chamber that can carry an electrical current. For example, the running buffer can be 0.01M $K_2SO_4$. The running buffer can comprise other agents, e.g., those useful for the maintaining the activity and/or stability of the biomolecule such as protease inhibitors or detergents. The running buffer used in the first dimension can be optionally changed to the same or different buffer in the second dimension step. Alternatively, no running buffer is present in the second dimension step. According to one embodiment, the running buffer is optimized for the pH range of the IEF buffers and biomolecule of interest to allow the complexes to accumulate in the appropriate cells. A running buffer can be adjusted to be a pH value that increases or decreases the mobility of a biomolecule entering an IEF buffer or cell.

A device for directing an electrical field through the IEF buffer or cell according to this invention can, e.g., include the use of a cathode electrode and an anode electrode and a voltage power supply. According to one embodiment, the device is capable of generating an alternating electric field. The electrodes can be placed on opposite sides of the IEF buffer or cell such that the electrical field passes into the IEF buffer or the cell. According to one embodiment of this invention, the electrodes are wires. According to another embodiment of this invention the electrodes are parallel sets of wires or thin plates. See e.g., FIGS. 2–6. The device can supply AC or DC voltage. If the IEF buffer or cell is in a closed system (e.g., the electrical field cannot pass through one side of the IEF buffer or cell and out the opposing side of the IEF buffer or cell), then it is advantageous that the device is capable of directing an electrical field in and out of the IEF buffer or cell comprising the IEF buffer (i.e., an alternating electrical field). The orientation of the alternating field does not have to be perpendicular to the plane of the array or the face plane of the IEF buffer or cell. It can be between +90 and −90 degrees relative to the plane of the array, always preserving a field component parallel to the axis of the IEF buffer or cell.

According to one embodiment, the electrodes are made of platinum or titanium or coated with platinum or titanium.

According to one embodiment of this invention, the electrodes are between 0.5 to 10 cm distance apart. According to another embodiment, the electrodes are 5 cm apart. According to a further embodiment, the distance between the electrodes is the minimal distance that still allows the running buffer to circulate across the cells. According to a further embodiment, the electrodes are approximately the same distance apart as the matrix or as the length of the cell.

The voltage applied to the running buffer can be DC or AC. If the IEF buffer or cell is closed and voltage applied is DC, then there must be a way for manually or automatically alternating the direction of the electrical field so that the electrical field is directed in and out of the IEF buffer or cell. According to an embodiment of this invention, the direction of the electrical field can be changed, e.g., by manually or automatically switching the polarity of the applied voltage or rotating the IEF buffer or cell by 180 degrees in a constant electric field. According to one preferred embodiment, the voltage is AC.

A device for circulating the running buffer across the IEF buffer or cell simultaneously includes, e.g., a stir bar placed in the chamber controlled by a magnetic plate or other devices for circulating liquid known in the art (e.g., pumps, vibrators, e.g., piezo vibrator, agitators, tilting devices). See FIG. 2. In another embodiment, the device for circulation can be a mechanism for moving the IEF buffer or cell relative to the running buffer. For example, the IEF buffer or cell can be rotated in the running buffer. The activity of such devices is useful during the first dimension step (IEF step) in the methods and systems of this invention. According to this invention, the circulation of the running buffer or cells relative to the running buffer promotes high rate of exposure of the biomolecules of interest to their respective IEF buffers or cells. Alternatively, the methods and systems of this invention can be devoid of such a circulating device. In another embodiment of this invention, the circulation is solely provided by the convection currents naturally generated during the isoelectric focusing. According to one embodiment of this invention, the amount of convection energy that is sufficient to circulate the biomolecule is $10^{-10}$ joules per 1 $cm^3$ of running buffer.

Figure 21:
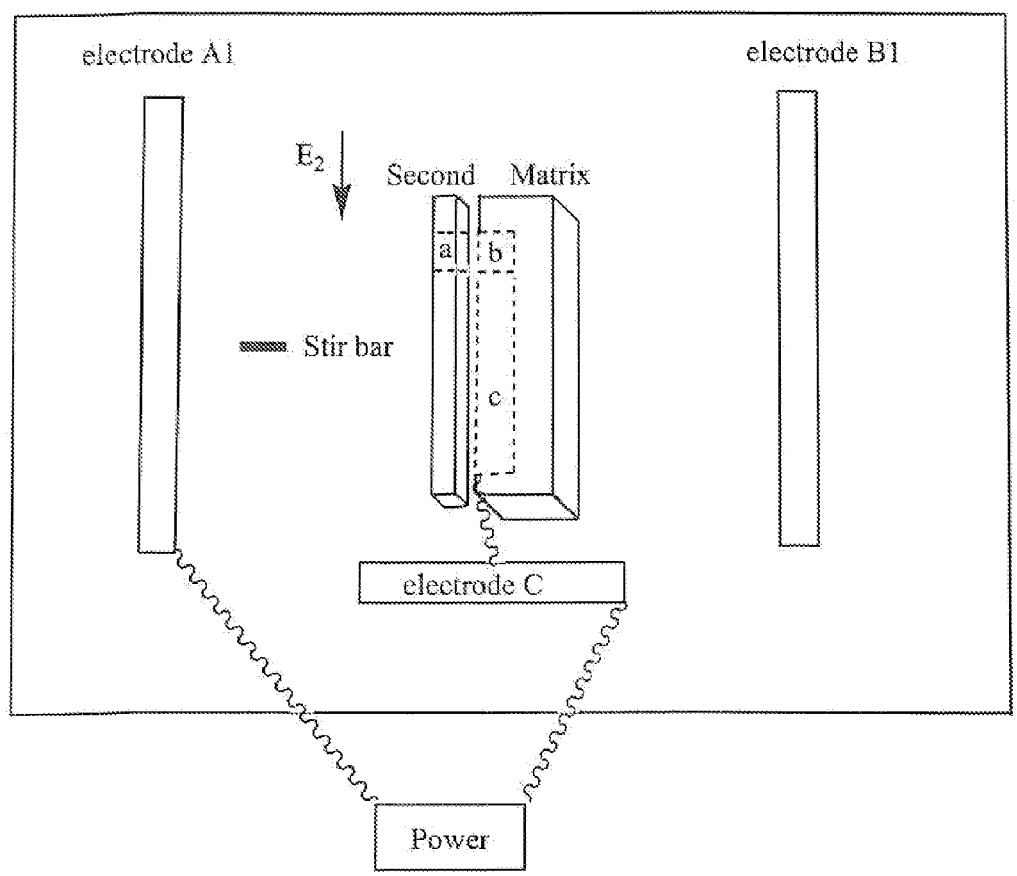
FIG. 21 is a diagram of an example of a three-electrode system according to this invention.

A device for directing an electrical field down the length of the lane away from the IEF buffer or the cell can comprise several different, arrangements of components. This device functions to move the biomolecules within the IEF buffer into and down the lane. Accordingly, the direction of the electric field in the second dimension that involved a lane separation should be predominantly away from the IEF buffer and down the lane. For example, one electrode can be place at one end of the IEF/lane unit (e.g., at the tip of the IEF buffer) and another at the other end of the IEF/lane unit (e.g., at the end of the lane). Alternatively, one electrode can be placed at the end of the lane and the other electrode can be one that was used in the prior IEF separation step. See e.g., FIG. 21. The voltage being supplied can be DC. Power supplies and electrodes that can supply a DC current are commercially available and known in the art.

A system according to this invention comprises several components that can be sold as a kit disassembled or assembled. Components of the kit include: an IEF buffer, cell, matrix or an array according to this invention; and optionally a device for directing an electrical field in and out of the IEF buffer and cell and/or a chamber comprising a running buffer. The system also optionally includes a device for directing an electrical field down the length of a lane away from the IEF buffer or cell. The system optionally further includes a device for circulating the running buffer across the IEF buffer or cell. An examples of a system according to this invention include FIG. 21. According to one embodiment of this invention, the chamber is disposable and has connectors that are attached to the bottom or side of the chamber to contact the voltage supply.

A system according to this invention may further comprise any one of the following: a device for detecting the biomolecules of the sample in a cell or lane; a device for receiving the data from the detection device; and a device for processing the data received. According to one embodiment, a scanning microdensitometer detects, receives and processes the signal from the cell(s) or lane(s).

One or more of the devices necessary for detecting the biomolecules of the sample in the cell or lane, receiving the data from the detection device, and processing the data received can be packaged into a computer.

A detection device can be designed to project electromagnetic radiation that is a spectrum of wavelengths, a plurality of wavelengths or one wavelength onto a lane simultaneously or sequentially. According to one embodiment, the illuminating light source is monochromatic. For example, the detection device can be a custom-made photometer that quickly, sequentially reads the absorption magnitude from each IEF buffer, cell or lane at a specific wavelength after a narrow spectrum of light is projected onto each IEF buffer, cell or lane. Alternatively, the detection device can be designed to read each IEF buffer, cell or lane simultaneously and/or take readings relating to the electromagnetic radiation emitted from each IEF buffer, cell or lane at several wavelengths.

Suitable detection devices, including, but not limited to, the naked eye, spectrophotometric, chemiluminescent, photometric/densitometric, electrochemical or radiochemical detecting instruments depending on whether the biomolecule is labeled and the type of label. The label can require other components to cause a reaction that produces a signal or to enhance the signal that is detectable according to the above-mentioned methods. A detailed discussion of suitable signal producing systems can be found in Ullman, et al., U.S. Pat. No. 5,185,243, columns 11–13, incorporated herein by reference. Details of techniques for attaching labels are known in the art. See, for example, Matthews, et al., Anal. Biochem. (1985) 151:205–209 and Engelhardt, et al., European Patent Application No. 0302175.

According to one embodiment of the invention, the computer contains a module that is capable of causing the computer to execute the steps of (a) receiving experimental data from the lane(s) and (b) generating a profile representative of the biomolecules in the sample and/or the biomolecules of interest in the sample. Such module can be useful in rapidly identifying, triaging and selecting more functionally annotated drug targets in disease. According to another embodiment of the invention, the computer contains a module that is capable of causing the computer to execute the steps of (a) receiving experimental data from the lane(s) and generating a profile of biomolecules in the sample; (b) receiving a reference profile; and (c) calculating an objective measurement of the similarity between the two profiles. The reference profiles can be values known in the art or values programmed by the researcher.

The computer can be linked to a network, which can be part of an Ethernet link to other local computer systems, remote computer systems, or wide area communication networks such as the Internet. The network link allows the computer to share data and processing tasks with other computer links. The access to shared data is particularly useful for genetic or proteome analysis for diagnostic, pre-diagnostic or general research purposes. For example, the computer can be preset to recognize particular profile (e.g., protein or RNA expression patterns) that is indicative of a particular disease state or susceptibility to a particular disease state using known information. Then, a sample from a subject can be tested using the system of this invention to determine if the biomolecules in the sample exhibit the same profile.

Figure 20:
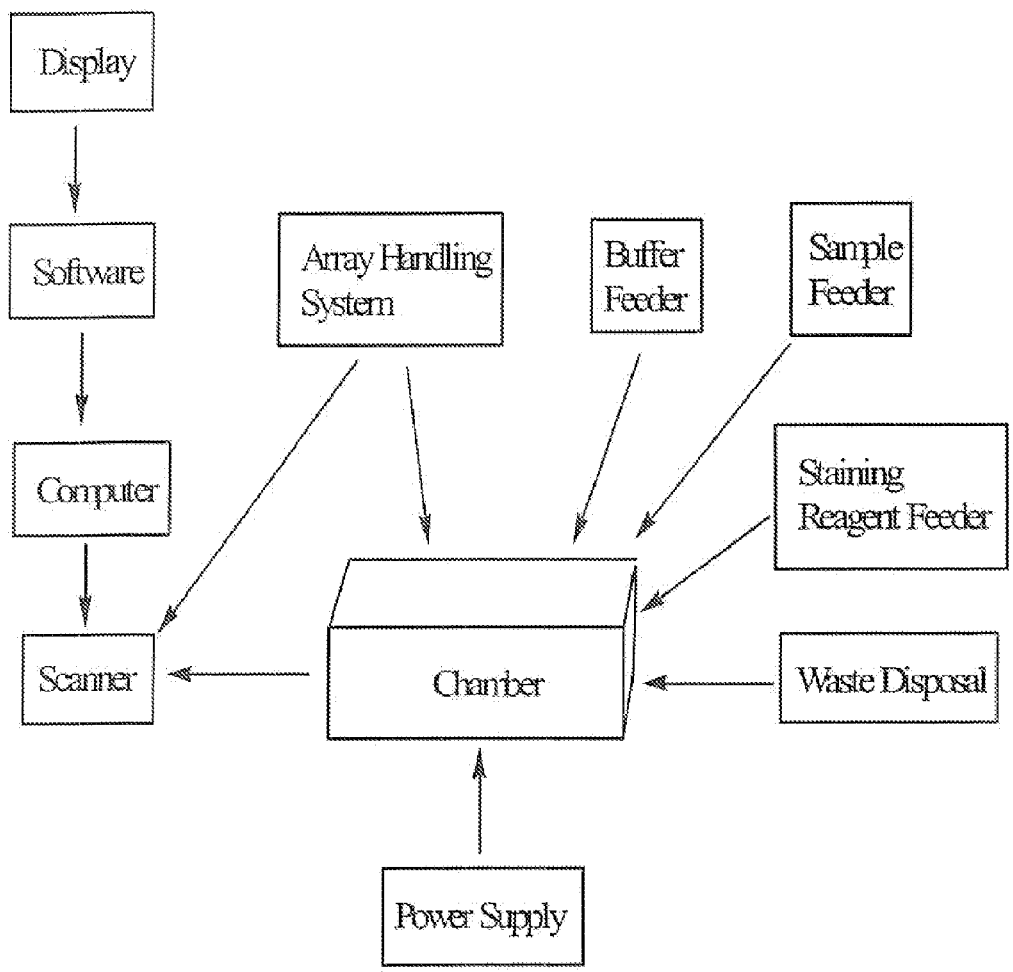
FIG. 20 is a schematic example of one automated system of this invention. The system provides, for example, a device for feeding a sample into the two dimensional electrophoretic analysis chamber of this invention ("sample feeder"), a device for removing waste ("waste disposal"), a device for adding new running buffer ("buffer feeder"), a device for staining the matrix after two dimensional analysis ("staining reagent feeder"), a device for bringing the stained chip to a scanner ("array handling system"), a device for scanning the chip ("scanner"), a device for receiving and recording the scanned image ("computer"), a device for analyzing the recorded image ("software"), and a device for displaying the recorded image ("display").

Further still, the system according to this invention can additionally include at least one, a combination or all of the following: a sample feeder, a waste disposal, a buffer feeder, a staining reagent feeder, an array handling system and a display. A sample feeder of this invention can be programmed to add an aliquot of a sample to the chamber. A waste disposal of this invention can be programmed to remove waste material (e.g., running buffer after its use) at any time during the analysis. A buffer feeder of this invention can be programmed to release new or different buffer at any time during the analysis. A staining reagent feeder can be programmed to release and expose the biomolecules to stain for a set period of time. An array handling system can be programmed to move the matrix, array or chamber as necessary during the analysis. A display according to this invention can be a screen or other device that provides information related to the results of the one or two dimensional analysis. See, e.g., FIG. 20.

According to one embodiment of the invention, the system is automated in whole or in part so that one or many samples can be analyzed according to the methods of this invention. For example, sample could be added to the system that is programmed to carry out all the steps of one-or two-dimensional analysis, to collect an image of the lanes and to receive, process and determine whether a specific biomolecule or pattern of biomolecules is present.

A system of this invention can be constructed to have additional, automated, interacting components, for example, titrators for filling channels with pH solutions or gels (immobilines, ampholyte mixtures etc.) and extractors for recovering biomolecules from the IEF buffers, cells or lanes. According to one embodiment, the system of this invention is automated for high throughput screening of samples, compounds or drugs.

Biomolecules according to this invention include any organic molecule present in a biological sample having a charge such as peptides, proteins, oligosaccharides, lipids, steroids, prostaglandins, prostacyclines, and nucleic acids (including DNA and RNA). As used herein, the term "biomolecule" includes unmodified, glycated, unglycated, phosphorylated, unphosphorylated and otherwise modified biomolecules. For example, a biomolecule of this invention can be labeled prior to separation in the first dimension (e.g., by $^{35}$S-methionine labeling or $^{32}$P-labeling). According to one embodiment of this invention, the biomolecules are proteins. According to another embodiment of this invention, a biomolecule can be man–made or naturally occurring. According to yet another embodiment of this invention, a protein is a peptide which can be of a length selected from the group consisting of, but not limited to, less than 500 residues, less than 300 residues, less than 200 residues, less than 100 residues, less than 50 residues, less than 25 residues, and less than 15 residues.

A target biomolecule ("TB") according to this invention is a biomolecule of interest that is specifically recognizable by a target recognition molecule ("TRM"). In one embodiment, the target biomolecule is a marker for a disease or condition. The target biomolecule can be a biomolecule that is endogenous to the sample or exogenous to the sample, i.e., added to the sample or running buffer. The biomolecule of interest can be modified so that it is a TB that has affinity or greater affinity to a TRM. For example, the biomolecule of interest can be covalently modified to additionally comprise a peptide containing an epitope that specifically binds to a TRM such as an antibody.

A TRM is a molecule that specifically binds to a portion of the TB. TRM can be useful for providing or amplifying a signal for detection and/or providing a signal distinguishable over background. For example, a TRM can be a labeled antibody that specifically recognizes the TB such as a monovalent (monoepitopic) or polyvalent (polyepitopic)) polyclonal antibody, a monoclonal antibody or an antibody fragment (e.g., Fab, Fv and F(ab')2, Fab', and the like). In addition, aggregates, polymers, and conjugates of immunoglobulins or their fragments can be used where appropriate so long as binding affinity for a particular target biomolecule is maintained. In the case where the target biomolecule is an antibody, antibodies that specifically bind that antibody can be used. In another example, the TRM can be a ligand or a receptor that binds to the TB when the TB is a receptor or a ligand, respectively. In yet another example, the TRM can be a single-stranded nucleic acid molecule that specifically binds to or hybridizes to TB when the TB is a nucleic acid molecule. Alternatively, the TRM can be a nucleic acid binding protein such as a transcription factor, splicing factor, histone or the like that binds to a nucleic acid molecule. In yet another example, a TRM can be a molecule that specifically binds to the active site of an enzyme when TB is that enzyme.

Accordingly, the TB and TRM can be selected from the group consisting of polynucleotides such as m-RNA, r-RNA, t-RNA, DNA, DNA-RNA duplexes; polynucleotide binding agents, such as, but not limited to restriction enzymes, activators, repressors, nucleases, polymerases, histones, repair enzymes, chemotherapeutic agents; antigens and antibodies; non-immunological pairs such as avidin and biotin; receptors and ligands including membrane bound receptors such as G-protein receptors (e.g., muscarinic, adrenergic, prostaglandin and dopamine such as the D2 receptor), tyrosine kinase (insulin-like IGF, epidermal EGF, nerve NGF, fibroblast FGF growth factors), ion channels and T-cell receptors.

The biomolecules can be tagged prior to the IEF separation step or after separation in the second dimension for detection by, e.g., the naked eye, spectrophotometric, chemiluminescent, photometric/densitometric, electrochemical or radiochemical means or by surface plasmon resonance imaging. The tag can be a detectable molecule such as a compound, nucleic acid or protein (e.g., antibody) that is labeled or is endogenously detectable and specifically recognizes the biomolecule. In the case where the biomolecule is tagged prior to the IEF separation step, the pI of the biomolecule will likely change because of the presence of the tag, thus the pH values of the IEF buffers or cells will change accordingly to capture the complex. See, e.g., U.S. provisional patent application No. 60/340,698, filed Oct. 29, 2001, incorporated by reference herein. The biomolecule can be tagged after the second dimension by methods known in the art such as, e.g., western blotting.

Several non-specific stains for biomolecules are known in the art and are useful for tagging the biomolecules according to this invention, e.g., coomassie blue, silver staining, Hoechst dye and 4', 6-diamidoino-2-phenylindole (DAPI). The stain and the tags used will vary according the biomolecule of interest.

Labels useful for detecting biomolecules can include fluorophores, substrates, electron transfer agents, coenzymes, enhancers, enzymes, substances that react with enzymic products, catalysts, activators, cofactors, inhibitors, scavengers, metal ions, and a specific binding substance required for binding of signal generating substances. Examples of a fluorophore useful according to this invention include fluorescein, cyanine dyes, coumarins, phycoerythrin, phycobiliproteins, dansyl chloride, isothiocyanate, rhodamine compounds, phycocyanin, allophycocyanin, o-phthaldehyde, and fluorescamine and Texas Red. Suitable labels include, by way of illustration and not limitation, enzymes such as alkaline phosphatase, glucose-6-phosphate dehydrogenase ("G6PDH") and horseradish peroxidase; promoters; dyes; electroluminescent labels such as ruthenium chelates; chemiluminescers such as isoluminol; sensitizers; coenzymes; enzyme substrates; radiolabels such as $^{125}I$, $^{131}I$, $^{14}C$, 3H, $^{57}Co$ and $^{75}Se$. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

According to one embodiment, an antibody developed against a biomolecule of interest is labeled with a fluorophore. According to one embodiment, the fluorophore is selected to have a high absorption coefficient at a specific wavelength or a high fluorescent yield.

According to one embodiment, label free detection (e.g., surface plasmon resonance) may be used to detect single biomolecules or complexes. For example, cells or matrices may sit upon a solid support within the chamber which has been biotinylated in a manner such that cells of varying pH ranges sit upon one or more biotin molecules. Target biomolecules or target recognition molecules may be modified to be bound to streptavidin and then introduced into the cells or into the running buffer. Complexes of the proper pI will diffuse into one or more cells bearing the proper pH and will form a tertiary complex with the present biotin molecules. Such binding can be detected by a surface plasmon resonance sensor underneath the solid state support, with the resonance signal detected and processed by said detection means.

A complex comprising a TB and a TRM, wherein the components of the complex are covalently or non-covalently bound to each other, can comprise only TB and TRM or additionally comprise other molecules, such as other biomolecules, metal ions, detection moieties or labels. The overall pI value of the complex will dictate whether the complex accumulates in a particular cell or in none of the cells of the apparatus. If there are a plurality of complexes of interest to be monitored in a single sample, then it is highly desirable that the complexes do not have the same pI values nor use the same label.

A sample according to this invention refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). A biological sample can be a biological fluid obtained from any site (e.g. blood, plasma, serum, urine, bile, synovial fluid, cerebrospinal fluid, amniotic fluid, semen, cervical mucus, sputum, saliva, gingival fluid, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis).

Alternatively, a sample can be obtained from any organ or tissue (including a biopsy or autopsy specimen) or may comprise cells (whether primary cells or cultured cells) or medium conditioned by any cell, tissue or organ. If desired, the biological sample can be subjected to preliminary processing, including preliminary separation techniques. For example, cells or tissues can be extracted and subjected to subcellular fractionation for separate analysis of biomolecules in distinct subcellular fractions, e.g. proteins or drugs found in different parts of the cell. See Deutscher (ed.), *Methods In Enzymology* vol. 182, pp. 147–238 (1990) (incorporated herein by reference in its entirety).

The matrix, arrays, systems and methods of this invention are useful for quickly determining the pI of a biomolecule by allowing the researcher to test different broad or narrow ranges of pH values. In one embodiment of this invention, a biomolecule of interest within a sample may be placed directly into a plurality of cells with different pH ranges and analyzed manually or automatically by means of the aforementioned detection devices and systems. In another embodiment of this invention, a biomolecule of interest within a sample may be placed directly into the running buffer with the IEF buffers/cells or lanes analyzed manually or automatically by means of the aforementioned detection devices and systems.

A biomolecule that has been sorted, separated, characterized, quantitated and/or compared to other molecules using the matrixes, arrays, systems and methods of this invention can be further evaluated by methods and commercial systems known in the art (e.g., silver-staining, immunostaining, high pressure liquid chromatography (HPLC), affinity chromatography, capillary electrophoresis, polyacrylamide electrophoresis, SDS-PAGE, centrifugation, gradient gel electrophoresis, isoelectric focusing techniques, excision of the protein-containing region followed by other methods of analysis known in the art, e.g., mass spectrometry, e.g., mass spectrometry (PE Biosystems, PerSeptive DE-STR MALDI-TOF-MS and Bruker Esquire Ion-Trap MS ). Unlike traditional IEF focusing followed by MALDI TOF spectrometry, the present invention allows the detection of small amounts of biomolecules. For instance, the present invention is capable of detecting a low femtomole amounts of protein, high attomole amounts of protein or 1–200 pg of protein in the standard range of 10–200 kD using silver-staining.

According to one embodiment, this can be achieved by performing a small scale two dimensional analysis using a 5 cm×5 cm matrix or smaller comprising IEF buffer/lane units, comparing the separated biomolecules to biomolecules that have been separated on a traditional, larger IEF focusing gel and using the smaller scale analysis to determine the location of the appropriate area to be excised on the traditional IEF focusing gel for further analysis by another technique (e.g., mass spectrometry). A special holder with magnifying glass and a customized cutter can facilitate the excision of the location containing the biomolecule of interest. The amount of protein in the excised portion can be estimated, e.g., by using an optical density calibration scale prepared by staining known amounts of biomolecule separated by the methods of this invention.

Thus, the present invention expands the range of detectable biomolecules by mass spectrometry and enables the analysis of proteins that tend to be expressed at low levels in the cell. Accordingly, a protein in the range of sub pico-gram quantities can be detected and visualized by mass spectrometry. The present invention provides an accurate and reproducible method for observing a biomolecule's pI value and its mass.

When the protein in the sample derived from blood or tissue sample is subjected to the methods of this invention, disease-specific proteins can be separated in one or two dimensions and the those proteins in the lanes can be evaluated by methods known in the art (e.g., silver-staining, immunostaining, high pressure liquid chromatography (HPLC), affinity chromatography, capillary electrophoresis, polyacrylamide electrophoresis, SDS-PAGE, centrifugation, gradient gel electrophoresis, isoelectric focusing techniques, excision of the protein-containing region followed by other methods of analysis known in the art, e.g., mass spectrometry, etc.).

Using the methods of this invention, one or more biomolecules can be focused according to pI, sorted, separated, purified, characterized, quantitated and/or compared to other biomolecules. The concentration of the biomolecules can increase or decrease in a sample or can be physically modified in response to an event. For example, the methods and systems of this invention can quantitatively and/or qualitatively monitor a change in a biomolecule in response to a disease state, drug treatment, life cycle, or other stimulus. For example, the phosphate modification of a protein or a protein level can be monitored before and after treating the protein or the environment around the protein with a stimulus. The system and methods of this invention can be used to observe the accumulation of the protein in a cell having a different pH value after treatment with the stimulus.

Anomalous expression of proteins in the sample from an animal or plant relative to a non-diseased animal or plant can be the hallmark of a specific disease. The relative abundance of biomolecules can be compared to a normal pattern for diagnosis or pre-diagnosis of a disease (e.g., cancer). The relative abundance of biomolecule in a cells can be normalized by introducing a known quantity of a specific protein into the sample before separation and comparing the optical density measurements to the optical density of the added protein. In an alternative embodiment, the appearance or disappearance or shift in the physical characteristics of a biomolecule in the test animal or plant compared to a normal animal or plant can be used to diagnose or pre-diagnose a diseased state. In yet another embodiment, the modification of a biomolecule in the test animal or plant compared to a normal animal or plant can used to diagnose or pre-diagnose a diseased state.

A diseased state according to this invention is any disease that can be detected by a change in a biomolecule in a sample (e.g., hemoglobin in diabetic subjects) or the deletion or addition of a biomolecule (e.g., proteins from bacterial infections). For example, the following genetic diseases can be diagnosed by a change in at the DNA or protein level: Huntington's disease, prostate cancer, Fragile X syndrome type A, myotonic dystrophy type I Kennedy's disease, Machado-Joseph disease, dentatorubral and pallidolyusian atrophy, and spino-bulbar muscular atrophy. The disease or condition also can be associated with a gene such as genes encoding BRCA1, BRCA2, APC; a gene encoding dystrophin, .beta.-globin, Factor IX, Factor VIIc, ornithine-d-amino-transferase, hypoxanthine guanine phosphoribosyl transferase, or the cystic fibrosis transmembrane receptor (CFTR); or a proto-oncogene. Examples of proteins that can be monitored are prostate specific antigens (PSA) for prostate cancer and cardiac enzymes for heart disease. Alternatively, a group of proteins can be monitored. In yet another embodiment of this invention, specific mRNA concentration profiles can be analyzed to determine a potential disease state.

In yet another alternative embodiment, the sample can be obtained from a cell culture or an in vitro assay that is cell-less. For example, samples from assays that comprise the use of cell fractions can be subjected to the one- or two-dimensional analysis of this invention before and after the cell fraction is perturbed by a drug or some other stimulus. In another embodiment of this invention, extracts from a developing organism or from the tissue of a subject can be analyzed to understand the changes that occur in the organism or animal during its life cycle. For example, compounds that are inhibitors, enhancers or initiators of a biological event can be identified. In all these assays, the TB and TRM can be added to the extract after a stimulus is applied to the extract, subject, or organism to be tested. In one embodiment, a method for high throughput screening of candidate molecules, including proteins and compounds, that cause a biological event comprising the step of detecting a TB or TBs in a sample using a system or method of this invention is contemplated.

According to an embodiment of this invention, the TRM can be added to the sample before or after the sample comprising the TB is added to the running buffer. According to one embodiment of this invention, the TRM is added to the sample comprising the TB before the sample is added to the running buffer. In all cases, it is most desirable to expose the TB and TRM to each other under conditions that will not inhibit or disrupt their binding to one another.

The term proteome refers to all the proteins expressed by a genome. Proteomics involves the identification and study of proteins in the body and the determination of their role in physiological and patho-physiological functions. The methods, matrixes, arrays and systems of this invention enable quicker, more sensitive techniques for monitoring the proteome. With this invention, more detailed and accurate functional proteomic maps of cellular activity can be developed, leading to a better understanding of diseases and discoveries of new medicines.

The term "monitor" as used herein is intended to include continuous measuring as well as end point measurement. In some embodiments, the biomolecules of the samples are measured continuously. In other embodiments, the biomolecules are analyzed before and after a cell or subject is stimulated or otherwise perturbed (e.g., by the addition of a drug or a change in the environment around the cell or subject). In still other embodiments, the biomolecules are measured in a control group of samples that have not been perturbed, and the cellular constituents of several experimental groups are measured and compared with those of the control group. It is apparent to those skilled in the art that other experimental designs are also suitable for the method of this invention to detect the change in biomolecules in response to perturbations.

The invention provides a method for sorting biomolecules in a sample away from each other. According to one embodiment of this method, a sample comprising the biomolecules is added to a system of this invention and circulated across an IEF buffer or cell, exposed to an alternating reversible electrical field in and out of the IEF buffer or cell; and then, optionally, separated in a second dimension, e.g., by exposing the biomolecules to an electric field that is directed down the lane away from the IEF buffer or cell.

The invention provides a method for characterizing a biomolecule in a sample. According to one embodiment of this invention, the biomolecule(s) of interest can be separated, prepared and/or analyzed in one dimension by adding the sample to the running buffer in an IEF apparatus of this invention, generating the electric field, circulating the running buffer, and periodically reversing the direction of the electric field. Alternatively, the sample could be added directly to the cell, channel, or lane. According to another embodiment of this method, a sample comprising the biomolecule is added to a system of this invention and circulated across an IEF buffer or cell, exposed to an alternating electrical field in and out of the IEF buffer or cell; separated in a second dimension, e.g., by exposing the biomolecules to an electric field that is directed down the lane away from the IEF buffer or cell and then determining the position or quantity of the biomolecule in the lane. The identification of the position or quantity of the biomolecule in the lane can be useful in determining the pI of the biomolecule, the molecular weight of the biomolecule and/or its state of modification. A change in the position of a biomolecule in a test sample compared to the same biomolecule in a control sample can be indicative of a modification of the biomolecule (e.g., phosphorylation, etc.). A change in the quantity of a biomolecule in a test sample compared to the same bimolecule in a control sample can be indicative of an increase or a decrease in the amount of the tested biomolecule due to, e.g., a change in the expression of the biomolecule or stability of the biomolecule.

The invention provides a method for quantitating the amount of a biomolecule in a sample using a matrix, array or system of this invention. The amount of a biomolecule in a lane according to this invention can be detected instruments known in the art as discussed above. Alternatively, the biomolecule in the lane can be bound with another molecule that is detectable by instruments known in the art. The quantity of the biomolecule can be extrapolated from a standard curve using known amounts of the same biomolecule or similar types of biomolecules (BSA for protein determination). The biomolecule in the lane can also be excised from the lane for analysis and quantitation.

According to one embodiment of this method, one biomolecule is monitored. According to another embodiment of this method, a plurality of biomolecules are monitored by a computer of this invention. According to a further embodiment of this invention, the data corresponding to the biomolecule or plurality of biomolecules of interest in the test sample are compared to the data corresponding to the biomolecule or plurality of biomolecules of interest from a subject that does not have the disease or is not predisposed to having the disease (i.e., a normal subject). It is desirable that computer according to this invention is able to compare and calculate the similarities and differences between the two sets of data. The parameters of the computer can be set to reach a threshold above which a positive or negative result is declared.

According to another embodiment, a system according to this invention can be used to remove biomolecules and/or ions in a sample away from a biomolecule of interest by adding the sample comprising the biomolecule of interest into a cell in the system. In this case, the IEF buffer in the cell would have a pH value(s) that encompassed the pI of the biomolecule of interest. Thus, if the reversible electric field and circulating means in the system are applied, other biomolecules or ions would migrate out of the cell but the biomolecule of interest would remain in the cell. The biomolecule of interest can be recovered from the IEF buffer or cell. Alternatively, a sample may be placed in a cell and an electric current passed through an IEF buffer or cell in a single direction, perpendicular to the plane of the biomolecule permeable walls of the buffer or cell.

An subject according to this invention includes a plant, animal or a human. In one embodiment, the subject is a human.

Throughout the specification, the word "comprise," or variations such as "comprises" or "comprising," will be understood to imply the inclusion of a stated integer or group of integers but not the exclusion of any other integer or group of integers.

All references, patents and patent applications cited herein are incorporated by reference. U.S. provisional application Nos. 60/305,802, filed Jul. 16, 2001; 60/310,316, filed Aug. 6, 2001; 60/340,698, filed Oct. 28, 2001 and 60/377, 044, filed Apr. 30, 2002 are incorporated by reference herein.

While a number of embodiments of this invention have been provided, it is apparent that the basic construction can be altered to provide other embodiments which utilize the compositions and methods of this invention. Therefore, it will be appreciated that the scope of this invention is encompassed by the embodiments of the inventions recited herein and the specification rather than the specific examples which are exemplified below.

EXAMPLE 1

Molecular Weight Standards

A groove of dimensions 0.1×0.1×3.0 mm was engraved in a thin para-methoxymethylamphetamine (PMMA) plate. The groove as filled with 10% SDS polyacrylamide gel. At one end of the lane, a spot of IEF buffer having an immobilized pH of 8.80 (arbitrarily chosen) was deposited. On hundred ngs of a protein ladder marker RPN 800 by Amersham Pharmacia Biotech (10 to 250 kD in molecular weight) were injected into the spot. A metallic electrode was connected to the immobilized pH gradient gel and another metallic electrode was connected to the end of the lane furthest away from the pH.

The plate was immersed in a 1%SDS 50 mM tris-glycine buffer (pH 8.3). A voltage of 36 Volts (field~100 v/cm) was applied to the electrodes for 5 minutes. Next, the lane was silver stained and fixed.

EXAMPLE 2

Two Dimensional Analysis of the Proteins of Blood Plasma at pH 8.65±0.05

A 100 micron diameter spot of a pH gel with pH value of 8.65±0.05 (polyacrylamide gel mixed with a buffer solution) was deposited on a polymer wafer, such as PMMA that is 1 cm×1 cm×0.3 mm. The wafer was placed in a small chamber comprising a stir bar and filled with 1M sodium sulphate buffer as a running buffer. 100 ng of blood plasma sample was introduced into the chamber (1 cm×1 cm×0.2 cm) comprising 200 ul of running buffer. A voltage of 50V was applied perpendicular to the plane of the wafer for 5 minutes width 180 degree changes in the direction of the current every 0.5 minutes. Next, the wafer was removed from the running buffer and rinsed in distilled water. The gel spot was removed from the wafer and placed at one end of a lane (10% SDS-PAGE) on a plate as described in Example 1.

The plate was immersed in a 1%SDS 50 mM tris-glycine buffer (pH 8.3). A voltage of 36 Volts (field~100 v/cm) was applied to the electrodes for 5 minutes. Next, the lane was silver stained and fixed.

EXAMPLE 3

Two Dimensional Analysis of Blood Plasma at pH 7.50 to 8.50

(1) The IEF Buffers

Fifty IEF buffers having pH values of 7.50 up to 8.50 in steps of 0.02 pH units were prepared.

a. IEF Buffers pH 7.50–7.68, 10% Polyacrylamide 25 mls 0.1M N-2-hydrosyethylpiperisine-N-3-propansulfonic acid (EPPS) (25,232 g/L) was mixed with 5 grams polyacrylamide (Biorad) and a volume of 0.1M NaOH as indicated below. The volume of the mixture was increased up to 50 mls with water at 25 degrees C.

| pH = 7.50 | 0.1 M NaOH 5.9 ml |
| pH = 7.52 | 0.1 M NaOH 6.1 ml |
| pH = 7.54 | 0.1 M NaOH 6.3 ml |
| pH = 7.56 | 0.1 M NaOH 6.7 ml |
| pH = 7.58 | 0.1 M NaOH 6.9 ml |
| pH = 7.60 | 0.1 M NaOH 7.0 ml |
| pH = 7.62 | 0.1 M NaOH 7.2 ml |
| pH = 7.64 | 0.1 M NaOH 7.3 ml |
| pH = 7.66 | 0.1 M NaOH 7.4 ml |
| pH = 7.68 | 0.1 M NaOH 7.5 ml | b. IEF Buffers Having pH 7.70–7.88, 7% Polyacrylamide 25 mls 0.1M N,N-bis(2-hydroxymethyl) glycine (BICINE) (16,317 g/L) was mixed with 3.5 grams polyacrylamide gel (Biorad) and a volume of 0.1M NaOH as indicated below. The volume of the mixture was increased up to 50 mls with water at 25 degrees C.

| pH = 7.70 | 0.1 M NaOH 6.5 ml |
| pH = 7.72 | 0.1 M NaOH 6.6 ml |
| pH = 7.74 | 0.1 M NaOH 6.7 ml |
| pH = 7.76 | 0.1 M NaOH 7.9 ml |
| pH = 7.78 | 0.1 M NaOH 7.2 ml |
| pH = 7.80 | 0.1 M NaOH 7.5 ml |
| pH = 7.82 | 0.1 M NaOH 8.7 ml |
| pH = 7.84 | 0.1 M NaOH 8.0 ml |
| pH = 7.86 | 0.1 M NaOH 8.2 ml |
| pH = 7.88 | 0.1 M NaOH 8.6 ml | c. IEF Buffers Having pH 7.90–8.26, 10% Polyacrylamide 50 mls 0.1M Tris-aminomethan (Tris) (12.114 g/L) was mixed with 7.0 grams polyacrylamide gel (Biorad) and a volume of 0.1M HCl as indicated below. The volume of the mixture was increased up to 100 mls with water.

| pH = 7.90 | 0.1 M HCl 34.5 ml |
| pH = 7.92 | 0.1 M HCl 34.3 ml |
| pH = 7.94 | 0.1 M HCl 34.1 ml |
| pH = 7.96 | 0.1 M HCl 34.0 ml |
| pH = 7.98 | 0.1 M HCl 33.6 ml |
| pH = 8.00 | 0.1 M HCl 36.5 ml |
| pH = 8.02 | 0.1 M HCl 33.2 ml |
| pH = 8.04 | 0.1 M HCl 33.0 ml |
| pH = 8.06 | 0.1 M HCl 32.9 ml |
| pH = 8.08 | 0.1 M HCl 32.7 ml |
| pH = 8.10 | 0.1 M HCl 32.5 ml |
| pH = 8.12 | 0.1 M HCl 32.2 ml |
| pH = 8.14 | 0.1 M HCl 32.0 ml |
| pH = 8.16 | 0.1 M HCl 31.8 ml |
| pH = 8.18 | 0.1 M HCl 31.7 ml |
| pH = 8.20 | 0.1 M HCl 31.5 ml |
| pH = 8.22 | 0.1 M HCl 31.3 ml |
| pH = 8.24 | 0.1 M HCl 31.2 ml |
| pH = 8.26 | 0.1 M HCl 31.1 ml |
| pH = 8.26 | 0.1 M HCl 30.8 ml | d. IEF Buffers Having pH 8.30–8.50, 8% Polyacrylamide 100 mls 0.04M 5,5-diethylbarbitural Na (veronal Na) was mixed with 8.9 grams polyacrylamide gel (Biorad) and a volume of 0.2M HCl as indicated below.

| pH = 8.30 | 0.2 M HCl 13.4 ml |
| pH = 8.32 | 0.2 M HCl 13.1 ml |
| pH = 8.34 | 0.2 M HCl 12.9 ml |
| pH = 8.36 | 0.2 M HCl 12.7 ml |
| pH = 8.38 | 0.2 M HCl 12.5 ml |
| pH = 8.40 | 0.2 M HCl 12.1 ml |
| pH = 8.42 | 0.2 M HCl 11.7 ml |
| pH = 8.44 | 0.2 M HCl 11.2 ml |
| pH = 8.46 | 0.2 M HCl 11.0 ml |
| pH = 8.50 | 0.2 M HCl 10.74 ml |

The IEF buffers were individually mixed with ammonium persulfate and deposited in parallel lines on a thin lucite chip, each line having a width and thickness of 100 micron and a length of 1 cm and a different pH. The dimensions of the chip on which the IEF buffers were deposited were 1.2 cm×1.2 cm.

(2) The Running Buffer

Five mls of a solution having the final concentration 7M Urea, 2.2M thiourea, 1.1% (w/v) tetradecanoylamidopropyldimethylammoniopropanesulfonate (ASB14), 10% (w/v) dimethylacetamide (DMAc), 0.55 mM ethylenediaminetetra-acetic acid (EDTA) in deionized and distilled water (ddH$_2$O) was mixed at 30° C. on a rotating table for 30 minutes until dissolved. Five mls ddH$_2$O was added if needed for dissolving. Next, 0.4 g amberlite was added and the solution was rotated at 32° C. for 10 minutes. The solution was then passed through a 0.45 μm syringe filter without creating foam. Next, the following ingredients were added with water to a final concentration of 2% citrate acid-citrate Na buffer (pH 4.0) (w/v), 2 mM Tri(2-carboxyethyl)phosphine hydrochloride (TCEP); 2 mM acrylamide; 1% glycerin. Final volume:10 ml. The final concentration of some of the components of the running buffer is as filed: 7.7M urea, 2.2M thiourea, 1.1% ASB14, 11% DMAc, 0.55 mM EDTA The pH of the running buffer was adjusted to 4.0 with hydrogen chloride.

(3) The First Dimension Separation: Isoelectric Focusing Step

To perform the first dimension separation (IEF), the chip having the deposited IEF buffers described in above was placed in a chamber between two electrodes that were spaced 1 cm apart. The chamber had a 2 ml volume capacity. However, in this step, it was only filled with an amount of running buffer such that an end of the lucite chip was submerged in running buffer to a depth of 0.2 mm. As a result, a small area at the ends of each of the lanes, but not the entire area of the lanes was submerged in the running buffer. One microgram of a human plasma protein mixture was added to the running buffer. An electric field was applied to the chip. The field was generated by a rectangular waveform of +80V to −80V and frequency or 1 HZ. During the 10 minutes, a stir bar was used to circulate the plasma proteins around the chamber and to the IEF buffers.

(4) The Second Dimension Separation: SDS-Polyacrylamide Electrophoresis

After performing the first dimension separation, the chip was reorientated in the chamber between two electrodes spaced 1.3 cm apart and submerged in the same running buffer in such a way that an electrical field generated between the electrodes would be parallel to the lanes and would be directed away from the area on the lanes where the proteins accumulated in the IEF step towards the opposite ends of the lanes. A 3% SDS solution was added to the running buffer for a final concentration of 2% SDS running buffer. Immediately after adding the SDS, the electric field was generated using 100V for approximately 5 minutes.

After the second dimension separation, the chip was immersed in a silver nitrite solution and exposed to UV light for fast silver staining. After silver staining, the chip was scanned by a commercial office scanner (UMAX ASTRA 2200). The scanned image was digitalized and enlarged 10 times. The use of matrixes, arrays, systems and methods of this invention yield much better results than traditional methods. The resolution and sensitivity of two dimensional IEF-SDS analysis is much improved.

EXAMPLE 4

Two Dimensional Analysis of Blood Plasma at pH 5.50 to 6.00

(1) The IEF Buffers

Twenty-five IEF buffers having pH values of 5.50 up to 6.00 in steps of 0.02 pH units were prepared.

a. IEF Buffers pH 5.50–5.72, 7% Polyacrylamide 25 mls 0.1M 2-(N-morfolin) ethanolsulfonic acid (MES) was mixed with 3.5 grams polyacrylamide gel (Biorad) and a volume of 0.1M NaOH as indicated below. The volume of the mixture was increased up to 50 mls with water.

| | |
|---|---|
| pH = 5.50 | 4.4 ml 0.1 M NaOH |
| pH = 5.52 | 4.8 ml 0.1 M NaOH |
| pH = 5.54 | 5.1 ml 0.1 M NaOH |
| pH = 5.56 | 5.3 ml 0.1 M NaOH |
| pH = 5.58 | 5.5 ml 0.1 M NaOH |
| pH = 5.60 | 5.7 ml 0.1 M NaOH |
| pH = 5.62 | 5.9 ml 0.1 M NaOH |
| pH = 5.64 | 6.0 ml 0.1 M NaOH |
| pH = 5.66 | 6.4 ml 0.1 M NaOH |
| pH = 5.68 | 6.35 ml 0.1 M NaOH |
| pH = 5.70 | 6.7 ml 0.1 M NaOH |
| pH = 5.72 | 6.8 ml 0.1 M NaOH | b. IEF Buffers Having pH 5.74–5.98, 9% Polyacrylamide 25 mls 0.1M tris(hydroxymethil)aminomethan-maleat (Tris-maleat) was mixed with 9 grams polyacrylamide (Biorad) and a volume of 0.2M NaOH as indicated below. The volume of the mixture was increased up to 100 mls with water.

| | |
|---|---|
| pH = 5.74 | 7.8 ml 0.2 M NaOH |
| pH = 5.76 | 7.9 ml 0.2 M NaOH |
| pH = 5.78 | 8.1 ml 0.2 M NaOH |
| pH = 5.80 | 8.2 ml 0.2 M NaOH |
| pH = 5.82 | 8.4 ml 0.2 M NaOH |
| pH = 5.84 | 8.8 ml 0.2 M NaOH |
| pH = 5.86 | 9.3 ml 0.2 M NaOH |
| pH = 5.88 | 9.8 ml 0.2 M NaOH |
| pH = 5.90 | 10.5 ml 0.2 M NaOH |
| pH = 5.92 | 11.6 ml 0.2 M NaOH |
| pH = 5.94 | 12.0 ml 0.2 M NaOH |
| pH = 5.96 | 12.5 ml 0.2 M NaOH |
| pH = 5.98 | 12.97 ml 0.2 M NaOH |

The IEF buffers were individually mixed with ammonium persulfate and deposited in parallel lines on a thin lucite chip, each line having a width and thickness of 100 micron and a length of 1 cm and a different pH. The dimensions of the chip on which the IEF buffers were deposited were 1.2 cm×1.2 cm.

(2) The Running Buffer

The running buffer was the same as described in Example 3.

(3) The First Dimension Separation: Isoelectric Focusing Step

To perform the first dimension separation (IEF), the chip having the deposited IEF buffers described in above was placed in a chamber between two electrodes that were spaced 1 cm apart. The chamber had a 2 ml volume capacity. However, in this step, it was only filled with an amount of running buffer such that an end of the lucite chip was submerged in running buffer to a depth of 0.2 mm. As a result, a small area at the ends of each of the lanes, but not the entire area of the lanes was submerged in the running buffer. One microgram of a human plasma protein mixture was added to the running buffer. An electric field was applied to the chip. The field was generated by a rectangular waveform of +80V to −80V and frequency or 1 HZ for 10 minutes. During the 10 minutes, a stir bar was used to circulate the plasma proteins around the chamber and to the IEF buffers.

(4) The Second Dimension Separation: SDS-Polyacrylamide Electrophoresis

After performing the first dimension separation, the chip was reorientated in the chamber between two electrodes spaced 1.3 cm apart and submerged in the same running buffer in such a way that an electrical field generated between the electrodes would be parallel to the lanes and would be directed away from the area on the lanes where the proteins accumulated in the IEF step towards the opposite ends of the lanes. A 3% SDS solution was added to the running buffer for a final concentration of 2% SDS in the running buffer. Immediately after adding the SDS, the electric field was generated using 100V for approximately 5 minutes.

After the second dimension separation, the chip was immersed in a silver nitrite solution and exposed to UV light for fast silver staining. After silver staining, the chip was scanned by a commercial office scanner (UMAX ASTRA 2200). The scanned image was digitalized and enlarged 10 times.

The use of the matrixes, arrays, systems and methods of this invention yield much better results than traditional methods. The resolution and sensitivity of two dimensional IEF-SDS analysis is much improved.

EXAMPLE 5

Two Dimensional Analysis Using an Array

An array containing one IEF/lane unit was constructed and used in a two dimensional separation according to this invention.

(1) The Array

A 10% polyacrylamide gel having 2% SDS was deposited as a narrow lane on a 1 mm thick Lucite wafer. The dimensions of the lane was 10 mm length, 0.1 mm width and 50 microns thick. The lane was then covered with a 100 micron thick cellophane layer that had a 200 micron diameter, circular perforation. The cellophane layer was aligned with the lane so that the circular perforation was positioned at one end of the lane.

An IEF buffer was prepared by mixing polyacrylamide gel, pH 7.00 buffer and ammonium persulfate to form a 7% polyacrylamide gel. The pH 7.00 buffer was prepared by mixing 50 ml of N-ethylmorfolin-HCl (Sigma) with 8 mls 1M HCl and 42 ml of water. A drop of IEF buffer was deposited in the perforation and allowed to solidify.

(2) The First Dimension Separation: Isoelectric Focusing

The array prepared as described above was placed in a chamber containing running buffer (pH 6.9), a stir bar and electrodes. The running buffer consisted of 1 $\mu M K_2SO_4$ mixed with HCl. A sample comprising 1 microgram of human plasma protein was added to the running buffer. A square waveform voltage of +30V to −30V and frequency of 1 Hz was generated for 8 minutes while the running buffer was circulated.

(3) The Second Dimension Separation: SDS-PAGE

For the second dimension separation, a DC voltage of 30 V was applied along the lane for 5 minutes. This was accomplished by detaching one of the electrodes used in the IEF step from the power supply, reattaching it to the end of the lane that is farthest from the IEF buffer and activating the electric field, etc., FIG. 21. In this case, although there is a small, undesirable electrical force that is not parallel to the lane, there is significantly more electrical force being applied down the lane in a direction away from the IEF buffer that allows significant and efficient separation of the proteins in the lane.

After the second dimension separation, the array was immersed in a silver nitrite solution to stain the lane. The lane was silver stained for three minutes under ultraviolet illumination.

EXAMPLE 6

Two dimensional Analysis Using Three Electrodes

An array as described in Example 5 was prepared.

(1) The First Dimension Separation: Isoelectric Focusing

The array placed in a chamber containing running buffer (pH 6.9), a stir bar and three electrodes. The running buffer consisted of 1 $\mu M K_2SO_4$ mixed with HCl. A sample comprising 1 microgram of human plasma protein was added to the running buffer. Using two electrodes that were parallel to the plane of the array, a square waveform voltage of +30V to −30V and frequency of 1 Hz was generated for 8 minutes while the running buffer was circulated.

(2) The Second Dimension Separation: SDS-PAGE

For the second dimension separation, a DC voltage of 30 V was applied along the lane for 5 minutes. This was accomplished by detaching one of the electrodes used in the IEF step from the power supply, reattaching it to the end of the lane that is farthest from the IEF buffer and activating the electric field, etc., FIG. 21. In this case, although there is a small, undesirable electrical force that is not parallel to the lane, there is significantly more electrical force being applied down the lane in a direction away from the IEF buffer that allows significant and efficient separation of the proteins in the lane.

After the second dimension separation, the array was immersed in a silver nitrite solution to stain the lane. The lane was silver stained for three minutes under ultraviolet illumination.

EXAMPLE 7

Separation of Protein Mixture Components Using Lucite Matrix

Twenty-five holes, 1 mm in diameter and 2 mm deep, were drilled into the face of a rectangular, plastic (Lucite) plate and filled with 2% agarose gel. The holes (hereinafter, "channels") were arranged in a grid-like fashion, approximately 3 mm distance from each other. One side of each channel was sealed with a protein ion transparent membrane made of commercial nylon membrane (ICN, Irvine Calif.).

Isofocusing buffers having a pH value corresponding to the isoelectric point (pI) of cytochrome C, deoxy-hemoglobin, hemoglobin $\alpha_2\beta_2$, C-phycocyanin, lentil lectin and ferritin (BioRad) were prepared. The channel buffers (hereinafter, "IEF buffers") were prepared by mixing either glycine, HEPES (N-2-hydroxyethylpiperasin-N'-ethansulfonic acid), tris(hydroxymethyl)aminmetan (THMAM), citrate acid, BICINE (N,N-bis(2-hydroxymethyl)glycine or β,β-dimethylglutaric acid (DMGA) with water and titrating each IEF buffer to a different pH using sodium hydroxide, hydrochloride or $Na_2HPO_4$. See Table I below.

TABLE I

IEF buffers and corresponding proteins

| Buffer No. | IEF Buffer Concentration (aq.) | Protein | pI of Protein | Color of the protein in buffer |
|---|---|---|---|---|
| 1 | 50 mM glycine; 14 mM NaOH | cytochrome C | 9.28 ± 0.02 | red |
| 2 | 50 mM HEPES 12 mM NaOH | dexoxi-hemoglobin | 7.07 ± 0.02 | brown red |
| 3 | 50 mM THMAM 44.6 mM HCL | hemoglobin $\alpha^+_2\beta^+_2$ | 7.2 ± 0.04 | red |
| 4 | 52 mM citrate acid 96 mM $Na_2HPO_4$ | C-phycocyanin | 4.65 ± 0.02 | blue |
| 5 | 50 mM BICINE 18 mM NaOH | lentil lectin | 8.2 ± 0.07 | colorless |
| 6 | 50 mM DMGA 40 mM NaOH | ferritin | 4.6 ± 0.05 | red |

Each vertical series of channels in the matrix were filled with 3 μl of one type of IEF buffer from Table I. The filled channels were sealed with a protein ion transparent membrane (same as described above).

The matrix comprising the channels and IEF buffers was placed between two platinum electrodes in a chamber having the internal dimensions 50 mm width, 100 mm height and 50 mm length. Each electrode had approximately the same dimensions as the matrix and was arranged in parallel geometry approximately 5 cm from each other. The chamber further comprised 50 mls of 0.01M $K_2SO_4$ running buffer such that the matrix and the electrodes were immersed in the running buffer. A stir bar was present in the chamber to ensure circulation of the running buffer across the channels. The chamber was placed on a magnetic stirrer.

One microgram of any one of the following proteins were added to the running buffer in the chamber: cytochrome C, deoxy-hemoglobin, hemoglobin $\alpha^+_2\beta^+_2$, C-phycocyanin, lentil lectin and ferritin (BioRad). While the proteins were being stirred in the chamber at 25° C., a voltage of 100V DC (E=20V/cm) was applied to the electrodes for 2 minutes. After this time, the direction of the electric field was reversed for another 2 minutes. This process was repeated 5 times.

Protein sorting of each of the proteins was observed by watching the accumulation of the protein into one of the vertical series (columns) of channels. Generally, protein sorting was complete within 10 minutes.

EXAMPLE 8

Figure 9:
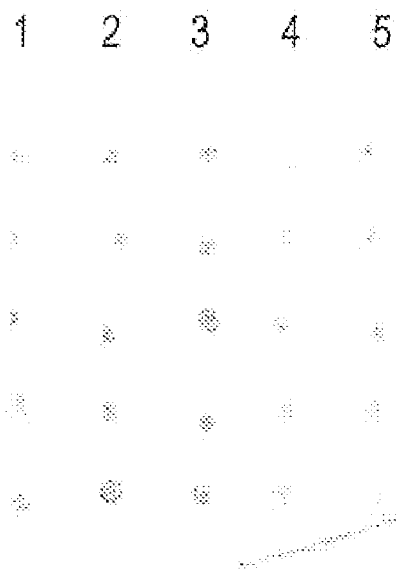
FIG. 9 depicts matrix of this invention comprised of an agarose gel with channels comprising a plurality of IEF buffers. Each vertical column of channels contain the same IEF buffer, except for the fourth column of channels which contain no buffer. Ferritin, phycocyanin (first band), phycocyanin (second band), and hemoglobin accumulated in the first, second, third and fifth vertical columns, respectively.
Figure 10:
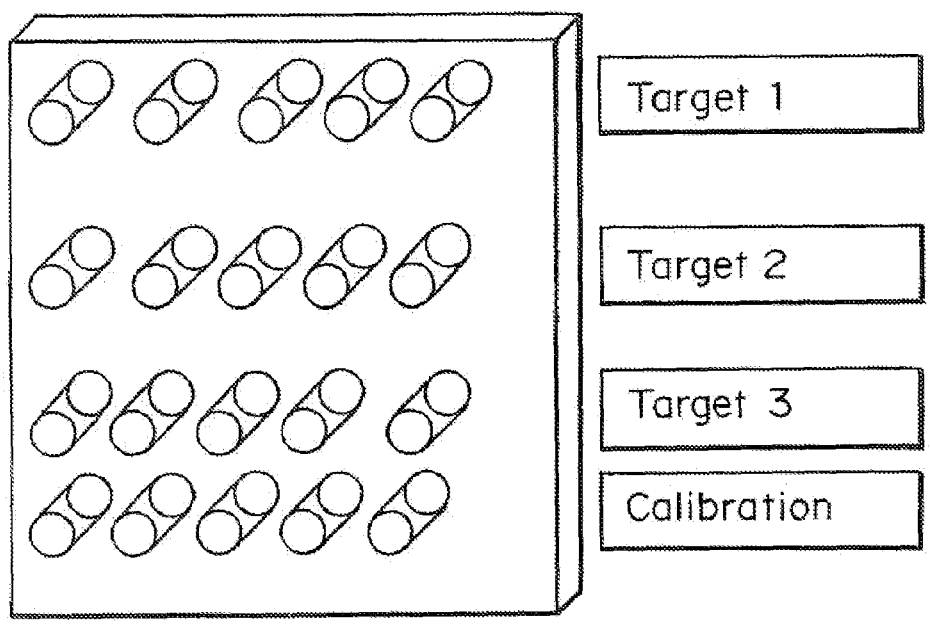
FIG. 10 is an image of a chip according one embodiment of this invention. The chip as drawn herein has been designed to analyze three target biomolecule in a sample. Each IEF buffer in each cell of the chip in the first, second and third rows has a pH that is the same as the pI of the complexes comprising various TBs/TRMs, e.g., TB1/TRM1, TB2/TRM2 or TB3/TRM3, respectively. The fourth row comprises cells that are designed to receive non-TB molecules that have been added to the running buffer for use as a control, standard or data point for developing a calibration curve. Accordingly, the IEF buffers in the fourth row have a pH value that is the same as the pI value of the non-TB biomolecule.

A 25-channel matrix was prepared as described in Example 7 except that each of the five vertical series of channels were filled with the following: buffer no. 6, buffer no. 4, and buffer no. 3, from Table I. See FIG. 9 from left to right, respectively. The matrix was then placed in a chamber with running buffer as described in Example 7. One microgram of ferritin, phycocyanin ($1^{st}$ band of the IEF standard in BioRad, Cat. No. 161-0310), phycocyanin ($2^{nd}$ band of the IEF standard in BioRad, Cat. No. 161-0310) and hemoglobin $\alpha^+_2\beta^+_2$ were added to the running buffer. While the proteins were being stirred in the chamber at 25° C., a voltage of 100V DC (E=20V/cm) was applied to the electrodes for 2 minutes. After this time, the direction of the electric field was reversed for another 2 minutes. This process was repeated 5 times.

Protein sorting of each of the proteins was observed by watching the accumulation of ferritin into the first vertical series of channels, phycocyanin ($1^{st}$ band) into the second vertical series of channels, phycocyanin ($2^{nd}$ band) into the third vertical series of channels, and hemoglobin $\alpha^+_2\beta^+_2$ into the fifth vertical series of channels. See FIG. 9. The negative control, i.e., the fourth vertical series of channels, showed no accumulation of any of the proteins. Furthermore, little or no accumulation of protein was observed in channels containing IEF buffers with pH values that did not correspond to the isoelectric points of the protein. Generally, protein sorting was complete within 10 minutes.

EXAMPLE 9

Method for Diagnosing Diabetes

A hallmark for the diagnosis of diabetes is an increase in the amount of glycated hemoglobin in the blood of the patient being tested. The quantity of glycated hemoglobin in the blood can expressed as a percentage ratio of the glycated hemoglobin to total hemoglobin. Accordingly, the concentrations of glycated hemoglobin (HbA1c) and non-glycated hemoglobin (HbA1) should be measured for diagnosing diabetes.

The pI of glycated and non-glycated hemoglobin was determined to be pH 6.95 and pH 7.22, respectively, using traditional IEF gel electrophoresis. Accordingly, a diagnostic chip containing two pH compartments, i.e., pH 6.95 and pH 7.22, was prepared.

The chip was made by drilling two holes, 2 mm in diameter and 1 mm deep, into the face of a rectangular, plastic (Lucite) plate and filled with 3% polyacrylamide gel. The holes (hereinafter, "channels") were arranged approximately 3 mm distance from each other. One side of each channel was sealed with a protein ion transparent membrane made of commercial nylon membrane (ICN, Irvine Calif.).

An isoelectric focusing buffer having a pH value of 6.95 was prepared by mixing 22.4 ml of 0.1M NaOH with 50 ml of 0.1M $KH_2PO_4$ and adding H2O for total volume of 100 ml. An isoelectric focusing buffer having a pH value of pH 7.22 was prepared by mixing 36 ml of 0.2M $Na_2HPO_4$ with 14 ml of 0.2M $NaH_2PO_4$ and adding $H_2O$ for total volume of 100 ml. The IEF buffers were mixed with acrylamide persulfate. The mixtures were added to separate channels and polymerized therein. The filled channels were sealed with a protein ion transparent membrane (same as described above).

Figure 2:
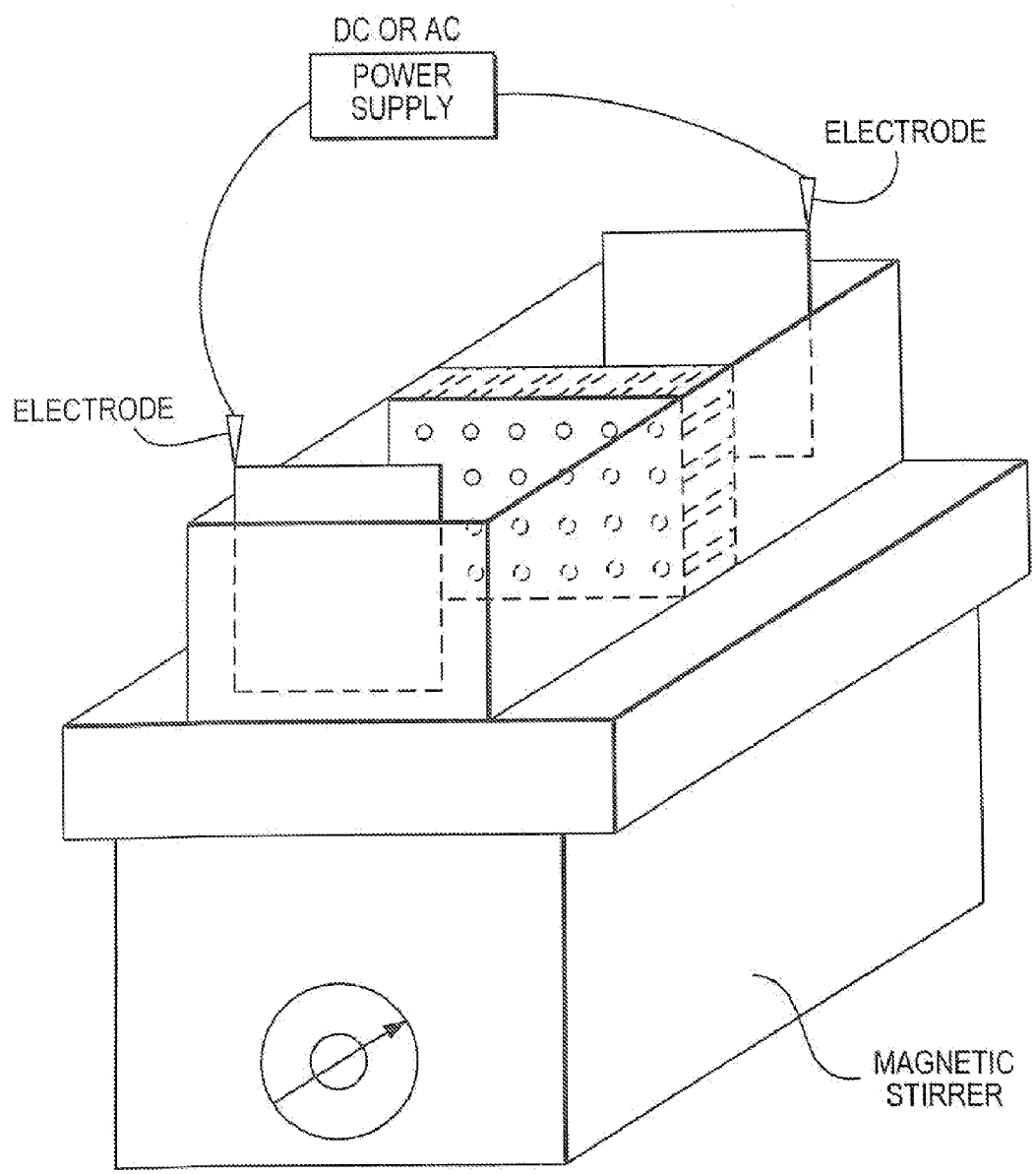
FIG. 2 depicts an apparatus of this invention comprising two electrode plates on either side of a chamber and a matrix comprising a plurality of cells in between the electrodes. The chamber is on top of a magnetic stirrer. The direction of the electrical field is reversible.
Figure 3:
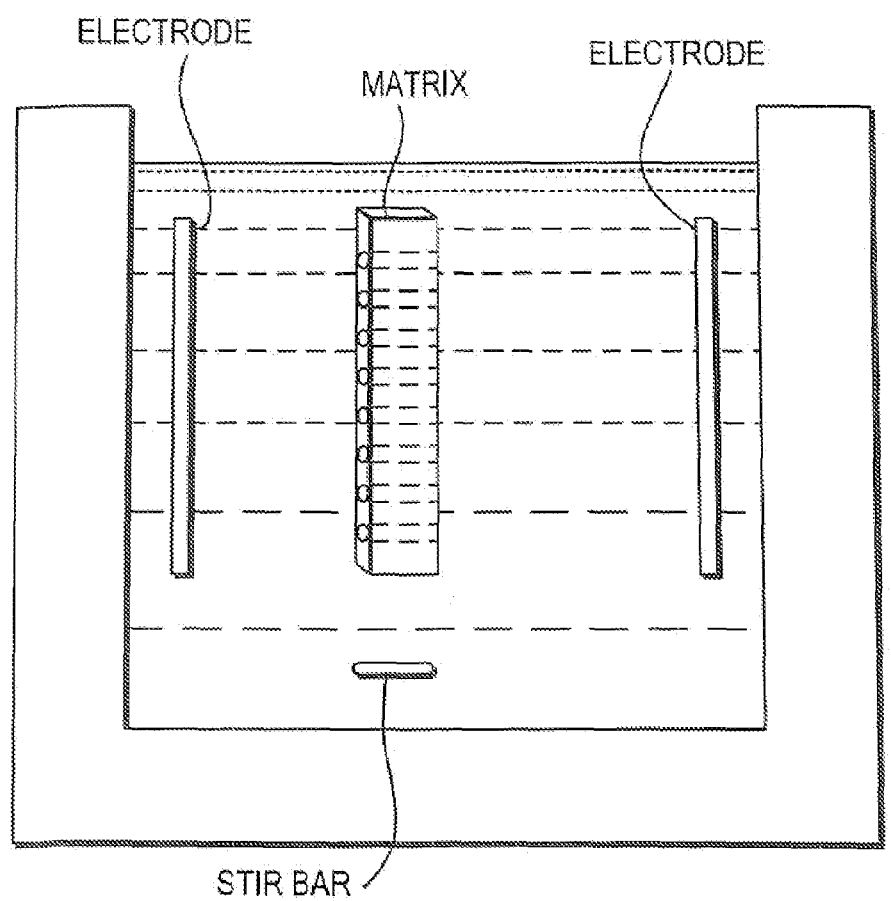
FIG. 3 depicts an apparatus of this invention comprising a matrix suspended over the bottom of the chamber between two electrode plates, wherein the running buffer can flow around the matrix aided by the stir bar. The direction of the electrical field is reversible.
Figure 4:
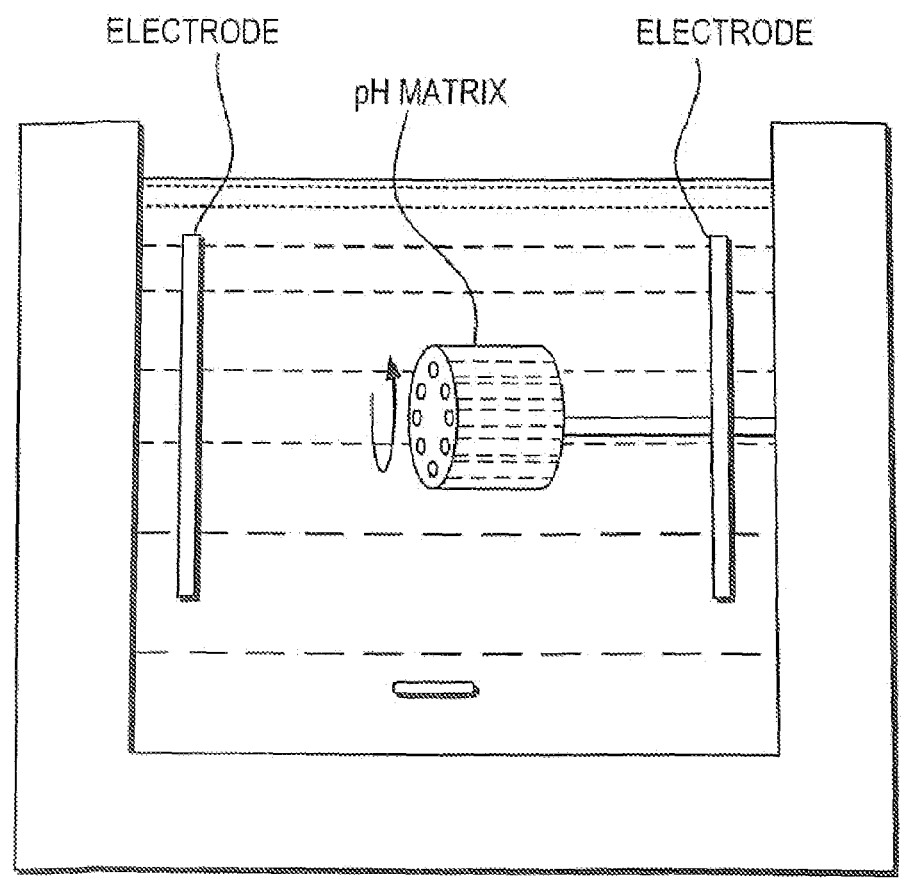
FIG. 4 depicts an apparatus of this invention wherein the matrix rotates to distribute the biomolecule in the running buffer across the cell openings. Optionally, the chamber may also have a stir bar to circulate the running buffer. The direction of the electrical field is reversible.

The chip was placed in separation chamber between two platinum electrodes as shown in FIG. 2. The internal dimensions of the separation chamber were 50 mm width, 100 mm height and 50 mm length. Each electrode had approximately the same dimensions as the matrix and was arranged in parallel geometry approximately 5 cm from each other. The chamber further comprised 10 mls of 10% HEPES buffer (pH 7.44) running buffer such that the matrix and the electrodes were immersed in the running buffer. A stir bar was present in the chamber to ensure circulation of the running buffer across the channels. The chamber was placed on a magnetic stirrer. The electrodes were attached to a power supply that could reverse polarity.

Figure 13:
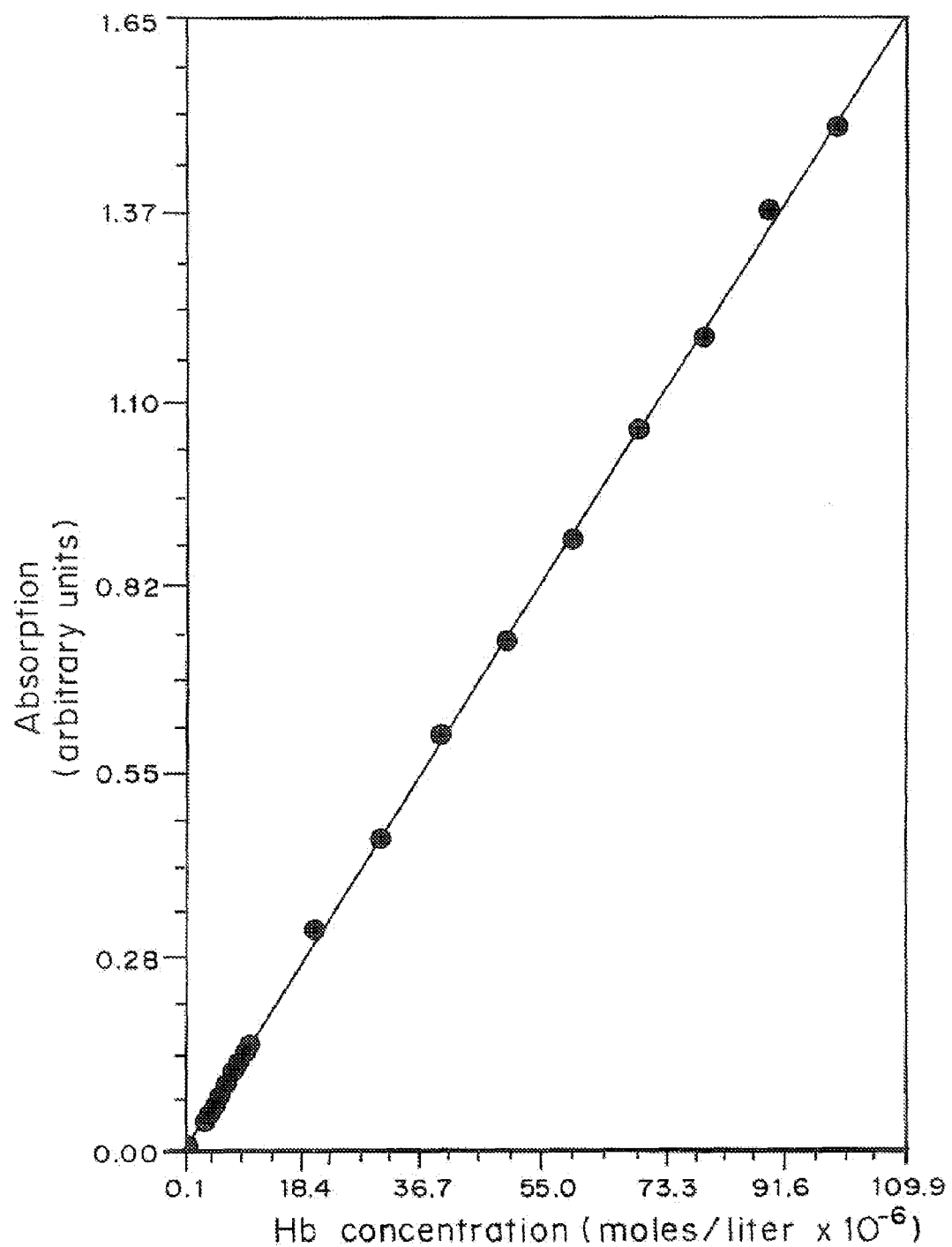
FIG. 13 is a graphical representation of the absorption of hemoglobin at 610 nm at various concentrations. Each data point represents a reading of absorption taken from a standard cuvette with rectangular shape filled with solutions having different concentrations of hemoglobin.

Glycated hemoglobin was purchased from Abbot [N1A86-10]. Non-glycated hemoglobin H-3883 was purchased from Sigma [9008-02-0], respectively, for use in forming calibration curves. Prior to preparing the mixtures of each for a calibration curve, the extinction coefficients of glycated and non-glycated hemoglobin were measured at several concentrations to confirm that they remained constant over the range used for the calibration curve. See,for example, Table 1 below and FIG. 13. The extinction coefficient for each was constant through two orders of magnitude of the concentration. The measurement was performed using a commercial spectrophotometer LKB 2202 made by Pharmacia.

| C (Mole/L) | Absorption (arbitrary units) |
| --- | --- |
| 1E-6 | 0.015 |
| 3E-6 | 0.044 |
| 4E-6 | 0.063 |
| 5E-6 | 0.077 |
| 6E-6 | 0.092 |
| 7E-6 | 0.107 |
| 8E-6 | 0.121 |
| 9E-6 | 0.138 |
| 1E-5 | 0.151 |
| 2E-5 | 0.317 |
| 3E-5 | 0.456 |
| 4E-5 | 0.611 |
| 5E-5 | 0.748 |
| 6E-5 | 0.901 |
| 7E-5 | 1.06 |
| 8E-5 | 1.196 |
| 9E-5 | 1.377 |
| 1E-4 | 1.497 |

To generate the calibration curve, six multicell chips each having two cells—a pH 6.95 and a pH 7.22 cell—were exposed to mixtures having different ratios of commercially available hemoglobin and glycated hemoglobin. For example, mixtures of glycate Hb to non-glycated Hb were resuspended in a constant volume of HEPES-NaOH (pH7.5). See Table 2. Absorbancy readings at 610 nm were taken for each cell. The percentage absorbance was calculated by dividing the absorbance reading for glycated hemoglobin by the sum of the absorbance reading for glycated hemoglobin and hemoglobin. The percentage concentration of glycated hemoglobin for each mixture (x-axis) was calculated by dividing the known molar concentration of glycated hemoglobin in each mixture with the sum of the total known molar concentration of glycated hemoglobin and non-glycated hemoglobin in each mixture. A line that is correlative to the percentage absorption vs. percentage concentration of glycated hemoglobin was drawn from the calculated data. The "x" marks where the percentage absorbance calculated from the absorbance readings for the sample at pH 6.95 and pH 7.22 occurs on the calibration curve. The percentage of glycated hemoglobin over total hemoglobin in the sample was extrapolated from the calibration curve. See Table 2.

Figure 14:
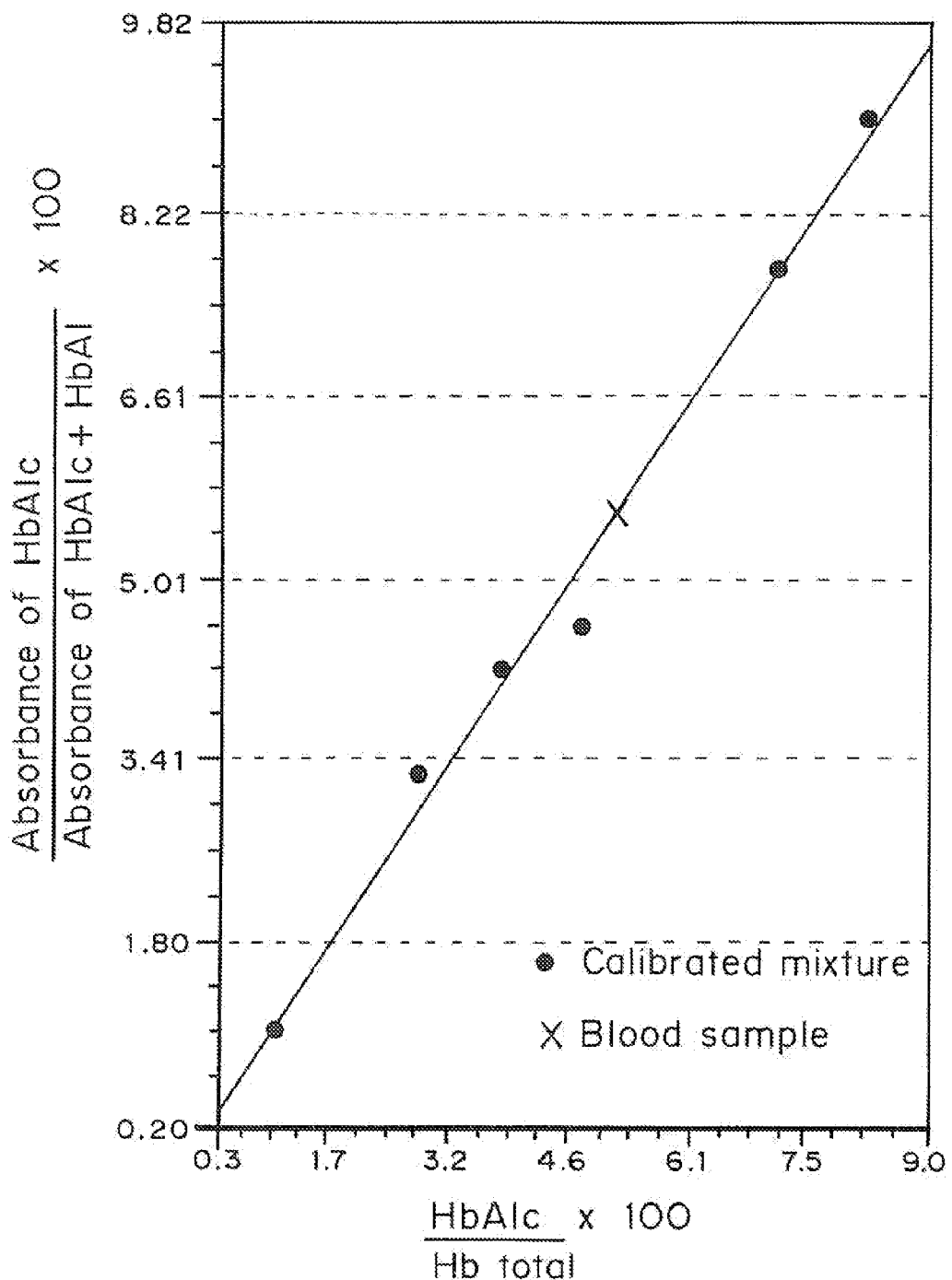
FIG. 14 is a graphical representation of a calibration curve for a blood sample being tested for diabetes. The X axis is the ratio of molar concentration of glycated hemoglobin to the sum of the molar concentration of glycated and non-glycated hemoglobin, expressed as a percentage. The Y axis is the ratio in percentage of the absorption of the glycated hemoglobin to the sum of the absorption of glycated and non-glycated hemoglobin.

Next, a sample of blood was taken from a patient. The blood was centrifuged at 500 g. A 10 ul aliquot of the supernatant was added to a chamber comprising a chip as described above and subject to 150 volts for 10 minutes. The percentage absorbance of glycated hemoglobin in the sample was calculated as described above ("Y" value). The percentage concentration of glycated hemoglobin for the sample was approximately 5.2% based on extrapolation from the line drawn in FIG. 14. This result indicates that the person being tested has diabetes. This percentage is typical for people with diabetes under control but is higher than the normal range of 3–4%.

EXAMPLE 10

Method for Determining Collection Efficiency for Isoelectric Focusing

As a means of determining the efficiency with which proteins are separated by the isoelectric focusing process of this invention, known quantities of Alexa Fluor 594 goat antimouse IgG (heavy and light chains; Jackson Immuno Research Laboratories; pI=8.2) were deposited into the running buffer of a system of this invention. The chamber contained a "separation chip": a single channel of a diameter

TABLE 2

Calibration using various concentrations of HbA1c and HbA1

| Conc. C1 HbA1c (moles/l) | Absorption (arb. units) | Conc. C2 HbA1 (moles/l) | Absorption (arb. units) | C1/(C1 + C2) (%) | A1/(A1 + A2) (%) |
|---|---|---|---|---|---|
| 1e-6 | 0.0157 | 1e-4 | 1.495 | 0.99 | 1.03 |
| 2e-6 | 0.037 | 7e-5 | 1.090 | 2.77 | 3.28 |
| 4e-6 | 0.661 | 1e-4 | 1.5 | 3.8 | 4.22 |
| 5e-6 | 0.070 | 1e-4 | 1.461 | 4.76 | 4.57 |
| 7e-6 | 0.111 | 9e-5 | 1.333 | 7.2 | 7.69 |
| 9e-6 | 0.141 | 1e-4 | 1.421 | 8.25 | 9.02 |

For each mixture, 10 ul of sample was added to a chamber comprising a chip as described above and subject to 150 volts for 10 minutes. The direction of the electrical field was reversed 1 time/minute. Hemoglobin has a strong absorption at 610 nm, which could be detected in this assay. Therefore, no TRM or label needed to be added to detect glycated or non-glycated hemoglobin.

The optical absorption of the glycated and non-glycated hemoglobin that accumulated in the pH 6.95 and pH 7.22 compartments, respectively, was measured using a spectrophotometer. The results were expressed as percentage concentration versus percentage absorbance of glycated hemoglobin to total hemoglobin (X vs. Y axis, respectively). See FIG. 14. Specifically, the percentage absorbance of the glycated hemoglobin in the tested mixture was calculated by dividing the absorbance reading from the pH 6.95 compartment by the sum of the absorbance readings from the pH 6.95 and pH 7.22 compartments and multiplying by 100. The percentage concentration of glycated hemoglobin for each mixture was calculated by dividing the known concentration of glycated hemoglobin in each mixture with the sum of the total known concentration of glycated hemoglobin and non-glycated hemoglobin in each mixture. A line that is correlative to the percentage absorption vs. percentage concentration of glycated hemoglobin could be drawn from the calculated data. See FIG. 14.

of 100 microns and a total volume of 1 nl. Each channel had an IEF buffer with a pH range of pH 8.2±0.05 pH units. The IEF buffer was made by mixing Tris Glycine (pH 8.20+/−0.05, Biorad, catalog number 161-0771) into a standard polyacrylamide gel.

To calibrate the system, 10,000, 50,000, 100,000, 300,000, 700,000, and 1,000,000 molecules of the above IgG were added to acrylamide and polymerized in individual pH 8.2 channels. Their fluorescence was measured with a Zeiss Axiovert 200 fluorescent microscope using Axiovision 2.05 to quantify the fluorescence intensity. A calibration curve of fluorescence intensity vs. concentration of the fluorescent marker was generated for comparison with experimental fluorescence intensities.

Next, 50,000, 100,000, and 1,000,000 molecules of the above IgG were tested in the above system. Each amount was individually deposited into a running buffer of a chamber. Isoelectric focusing was performed for each amount under fixed separation conditions using identical separation chips as described above (10 minutes through the narrow pH channels in 0.1 ml of a Tris Glycine (pH 4.8) buffer at 30V DC current). After each experiment, the fluorescent intensity was measured with the Zeiss Axiovert 200 fluorescent microscope and compared with the calibrated results.

The results shows that the collection efficiency of the process is close to 100% with a correlation coefficient of r=0.9999, indicating that almost all of the proteins are separated into their pH chambers in during the 10 minute duration of the experiment. See FIG. 22. The S value for the fit was 45.85. The abscissa represents the fluorescence value measured in the calibration run while the ordinate represents the fluorescence obtained after the isoelectric focusing runs. The numbers represent the total number of protein molecules in the sample demonstrating the high sensitivity of isoelectric focusing in narrow pH channels.

We claim:

1. A matrix for isoelectric focusing (IEF) comprising at least two compartments or cells that are not adjoined, the compartments or cells containing a first IEF buffer and at least a second different IEF buffer for use with a running buffer that circulates through and around the IEF buffers, not through one IEF buffer directly into another IEF buffer.

2. The matrix according to claim 1, wherein the IEF buffers have a pH range of 0.02 pH units or less.

3. The matrix according to claim 1, wherein the first IEF buffer and the second IEF buffer have a pH step of 0.1 pH units or less.

4. The matrix according to claim 3, comprising at least two IEF buffers in compartments or cells isolated from each other when ranged in a line perpendicular to an electrical field.

5. The matrix according to claim 3, wherein the at least two IEF buffers in compartments or cells are arranged in parallel to each other and in parallel to the direction of an electrical field.

6. The matrix according to claim 3, wherein the compartments or cells are imbedded in a matrix.

7. The matrix according to claim 1, comprising molecule impermeable areas.

8. The matrix according to claim 1, comprising ion impermeable areas.

9. The matrix according to claim 1, in a system further comprising a device for circulating running buffer across the IEF buffer or cell.

10. The matrix according to claim 1, comprising a polyacrylamide gel.

11. A system comprising:
  (a) a chamber comprising running buffer;
  (b) a matrix for isoelectric focusing (IEF) comprising at least two compartments or cells containing a first IEF buffer and at least a second different IEF buffer wherein the running buffer circulates around the IEF buffers rather than only through one IEF buffer directly into another IEF buffer; and
  (c) a device for generating an alternating electrical field in and out of the IEF buffer or cell.

12. The system of claim 11 wherein the matrix is moveable within the chamber.

13. The system of claim 11 wherein the electrical field is generated from an AC voltage device.

14. The system of claim 11 wherein the electrical field is generated from a DC voltage device.

15. A method for isoelectric focusing of a molecule in a sample comprising the steps of:
  (1) subjecting the sample in a running buffer to an electrical field that is directed in and out of a matrix for isoelectric focusing (IEF) comprising at least two compartments or cells containing a first IEF buffer and at least a second different IEF buffer wherein the running buffer circulates around the IEF buffers rather than only through one IEF buffer directly into another IEF buffer; and
  (2) trapping the molecule in an IEF buffer or cell.

16. The method of claim 15 wherein the IEF buffers have a pH range of 0.1 pH unit or less.

17. The method of claim 16, for characterizing a molecule in a sample comprising the steps of:
  (1) subjecting the sample to an electrical field that is directed in and out of the IEF buffer or cell and circulating a running buffet comprising the sample across the IEF buffer or cell; and
  (2) determining if the molecule is present in the IEF buffer or cell.

18. The method of claim 17 further comprising comparing the molecule in the IEF buffer or cell to a molecule from another sample or quantitating the molecule.

19. The method of claim 18, for diagnosing or prediagnosing a disease state in a subject comprising the step of comparing a molecule from a subject to be diagnosed or suspected to be predisposed to a disease state with a molecule from a sample from a normal subject that does not have a disease or is not predisposed to having the disease.

20. The method of claim 19 for diagnosing or prediagnosing a disease state in a subject comprising the steps of:
  (a) adding a sample comprising molecules from the subject suffering from a disease state or a suspected to be predisposed to a diseased state to the running buffer,
  (b) generating an electrical field;
  (c) generating the electrical field down from the IEF buffer or cell to form a pattern of molecules; and
  (d) comparing the pattern of molecules in the lane to a pattern of molecules from a sample from a normal subject that does not have the disease or is not predisposed to having the disease.

21. The method of claim 17, for preparing a molecule comprising trapping the molecule in IEF buffer or cell by generating an electrical field in and out of the IEF buffer or cell and, circulating a running buffer comprising the molecule across the IEF buffer or cell and recovering the molecule.

22. The method according to claim 17, further comprising the step of subjecting the molecule to a second dimensional analysis.

23. The method according to claim 22, wherein the second dimensional analysis is by polyacrylamide gel electrophoresis (PAGE), Mass spectrometry, capillary electrophoresis, or liquid chromatography.

24. The method of claim 15 wherein the electrical field is generated from an AC voltage device.

25. The method of claim 15 wherein the electrical field is generated from a DC voltage device.

26. The method of claim 15 wherein the electric field is perpendicular to the IEF buffers or cells.

27. The method of claim 15 wherein the IEF buffers are immobilized.

* * * * *

UNITED STATES PATENT AND TRADEMARK OFFICE
CERTIFICATE OF CORRECTION

| | | |
|---|---|---|
| PATENT NO. | : 7,166,202 B2 | Page 1 of 1 |
| APPLICATION NO. | : 10/198071 | |
| DATED | : January 23, 2007 | |
| INVENTOR(S) | : Shumel Bukshpan and Gleb Zilberstein | |

It is certified that error appears in the above-identified patent and that said Letters Patent is hereby corrected as shown below:

Column 35, line 23, replace "ranged" with --arranged--.
Column 36, line 13, replace "buffet" with --buffer--.
Column 36, line 29, replace "a suspected" with --suspected--.
Column 36, line 49, replace "Mass" with --mass--.

Signed and Sealed this

Fourth Day of September, 2007

JON W. DUDAS
*Director of the United States Patent and Trademark Office*